(12) United States Patent
Itsuki et al.

(10) Patent No.: US 7,196,211 B2
(45) Date of Patent: Mar. 27, 2007

(54) HAFNIUM-CONTAINING MATERIAL FOR FILM FORMATION, METHOD FOR PRODUCING THE SAME, AND METHOD FOR PRODUCING HAFNIUM-CONTAINING THIN FILM USING THE SAME

(75) Inventors: Atsushi Itsuki, Ibaraki (JP); Nobuyuki Soyama, Ibaraki (JP); Akio Yanagisawa, Ibaraki (JP)

(73) Assignee: Mitsubishi Materials Corporation, Tokyo (JP)

(*) Notice: Subject to any disclaimer, the term of this patent is extended or adjusted under 35 U.S.C. 154(b) by 239 days.

(21) Appl. No.: 10/939,314

(22) Filed: Sep. 9, 2004

(65) Prior Publication Data

US 2005/0065358 A1   Mar. 24, 2005

(30) Foreign Application Priority Data

| Sep. 19, 2003 | (JP) | ............................. 2003-327403 |
| Jan. 21, 2004 | (JP) | ............................. 2004-012742 |
| Mar. 29, 2004 | (JP) | ............................. 2004-094232 |
| Jul. 8, 2004 | (JP) | ............................. 2004-202195 |

(51) Int. Cl.
*C07F 7/00* (2006.01)
*C23C 16/00* (2006.01)

(52) U.S. Cl. ................. 556/51; 556/54; 427/248.1; 427/255.19; 427/255.32

(58) Field of Classification Search ............... 556/51, 556/54; 427/248.1, 255.19, 255.32
See application file for complete search history.

(56) References Cited

OTHER PUBLICATIONS

Office Action (Notice of Grounds for Rejection) issued from the Japanese Patent Office dated Mar. 16, 2005.
Patent Abstracts of Japan for JP2002-249455 published Sep. 6, 2002.
Patent Abstracts of Japan for JP2002-093804 published Mar. 29, 2002.
"Description of the circumstances requiring accelerated examination" filed Feb. 18, 2005 with the Japanese Patent Office.
Patent Abstracts of Japan for JP11-335310 published Dec. 7, 1999.
Patent Abstracts of Japan for JP2002-069027 published Mar. 8, 2002.

*Primary Examiner*—Porfirio Nazario-Gonzalez
(74) *Attorney, Agent, or Firm*—Darby & Darby

(57) ABSTRACT

A hafnium-containing material is presented for forming a film having excellent vaporization stability and higher film formation rate. Also a method for producing the film is presented. The hafnium-containing material for film formation has a bond of a hafnium atom with a nitrogen atom, or a bond of a hafnium atom and an oxygen atoms. Zr content contained in the material is equal to or less than 650 ppm.

20 Claims, 6 Drawing Sheets

US 7,196,211 B2

HAFNIUM-CONTAINING MATERIAL FOR FILM FORMATION, METHOD FOR PRODUCING THE SAME, AND METHOD FOR PRODUCING HAFNIUM-CONTAINING THIN FILM USING THE SAME

CROSS-REFERENCE

This application claims the benefit of Japanese application no. 2003-327403 filed Sep. 19, 2003, Japanese application no. 2004-12742 filed Jan. 21, 2004, Japanese application no. 2004-94232 filed Mar. 29, 2004, and Japanese application no. 2004-202195 filed Jul. 8, 2004. All priority applications above are incorporated herein by reference.

BACKGROUND OF THE INVENTION

1. Field of the Invention

The present invention relates to a hafnium-containing material for film formation as a source suitable for producing a hafnium-containing thin film useful as paraelectric thin film, optical thin film, catalyst thin film, solid electrolyte thin film and the like and a method for producing the same, and to a process for producing the hafnium-containing thin film made of the material produced by the above method. More specifically, the present invention provides a material useful for forming a hafnium-containing thin film such as Si—O—Hf thin film, $HfO_2$ thin film, etc., preferable as a source for producing a hafnium-containing thin film by metal organic chemical vapor deposition process (hereinafter, abbreviated as "MOCVD process"), a method for producing the same, and a process for production of a hafnium-containing thin film using the produced film forming material.

2. Description of the Related Art

Silicon oxide film has been widely known and has been commonly used as high-dielectric gate insulation film. Recently, film thickness of the silicon oxide film tends to be thinner as semiconductor devices become more highly integrated. If a silicon oxide (hereinafter, abbreviated as "$SiO_2$") film having the thickness of 100 nm or less is used, reduced insulation effect due to tunnel current flowing across the thin film typically occurs, which poses a limitation in obtaining films thinner than such thickness to suitably function as the insulation film.

In view of the above, a novel gate insulation film is required in replacing of $SiO_2$ film such as a hafnium-containing thin film, more particularly, $HfO_2$ or $HfO_2$—$SiO_2$ as a substitute for $SiO_2$ film. One of conventional methods for producing such thin films, MOD process such as sputtering, ion-plating or applied-pyrolysis, sol-gel method has been known. However, as a result of considering a variety of characteristics such as composition control, step coverage, conformity with processes for production of semiconductor device, etc., MOCVD process is being considered lately as an ideal film formation method.

Moreover, hafnium tert-butoxide (hereinafter, referred to as $Hf(OtBu)_4$) or hafnium tetrakis dipivaloylmethanate (hereinafter, referred to as $Hf(DPM)_4$) having coordinate covalent bonds with 2,2,6,6-tetramethyl-3,5-heptanedione residue (hereinafter, referred to as DPM) is attracting attention as the material for forming hafnium-containing thin film. However, $Hf(OtBu)_4$ shows poor reproducibility when the thin film is formed at low temperature while $Hf(DPM)_4$ has a disadvantage of forming film at high temperature in spite of good stability.

In order to solve the problems mentioned above, $Hf(DPM)_4$ obtained by adding Hafnium and purified dipivaloylmethane in an organic solvent purified and dehydrated under inert gas atmosphere, directly reacting the obtained solution together with reflux and heating followed by cooling the reacted product to be extracted, and by sufficiently purifying the resultant crude crystalline product by means of recrystallization is disclosed(for example, see Japanese Unexamined Patent Application Publication No. 2002-249455 (Patent Document 1)). As a result of purification by the above process, obtained is high-purity Hf complex containing 0.01 wt.ppm or less of metal impurities and with a purity of 99.99999% by weight or more.

Further, it has been disclosed a process for forming Hafnium-containing thin film using MOCVD process, which comprises steps of introducing at least one or multiple organic source material(s) represented by $M[N(C_2H_5)_2]_4$ wherein M is a metallic element, typically containing Si; depositing metallic film or metal compound film using CVD process; and conducting heat treatment for the deposited product at a desired temperature higher than the deposition temperature after the deposition step (for example, see Japanese Unexamined Patent Application Publication No. 2002-167672 (Patent Document 2)). By this process, film side of a semiconductor device and/or electronic device is deposited with metal component and compound thereof with excellent control and uniformity even when there is unevenness on the film side, thereby making it possible to achieve production of the semiconductor device and/or electronic device having improved characteristics.

However, Patent Document 1 still has a disadvantage of forming film in high temperature owing to a source material, that is, although $Hf(DPM)_4$ provides hafnium-containing thin film with excellent property by using a source material of high-purity, adverse effects are imparted to a substrate caused by the heating process.

Furthermore, the conventional technologies illustrated above have a problem in that the compounds such as $Hf(OtBu)_4$, $Hf(DPM)_4$ described in Japanese Unexamined Patent Application Publication No. 2002-249455 or $M[N(C_2H_5)_2]_4$ described in Japanese Unexamined Patent Application Publication No. 2002-167672 did not initially include zirconium element (Zr), but contained Zr as one of impurities during the synthetic reaction. This is because Zr has specific chemical structure and/or behavior substantially identical to Hf, making it difficult from being easily removed. If Zr as the inevitable impurity is contained in the material for forming hafnium-containing film, it causes the material to have poor volatility and decreases the film formation rate, or it deteriorates step coverage of the hafnium-containing thin film.

SUMMARY OF THE INVENTION

The present invention is designed in consideration of the problems of the above-mentioned prior art references, and has an object of providing a Hafnium-containing material useful for film formation with excellent vaporization stability and higher film formation rate and a method for producing the same.

Another object of the present invention is to provide a process for producing a hafnium-containing thin film with excellent step coverage.

One implementation of the invention is a hafnium-containing material for film formation comprising an organohafnium compound, in which the content of zirconium element contained in the material is 650 ppm or less.

Although Zr is generally known to be contained in an amount of at least 1000 ppm or more in the material as the inevitable compound to inhibit increase of film formation rate, the above invention defines the content of Zr to be 650 ppm or less so that it can control vaporization and pyrolysis characteristics. Thus, when the inventive material for forming a film is applied to form the film, it accomplishes excellent vaporization stability and enhancement of the film formation rate.

Another implementation of the invention is the material in which the organohafnium compound has a bond of a hafnium atom with a nitrogen atom.

Another implementation of the invention is the material in which the organohafnium compound is represented by the following formula 1:

$$Hf(R^1R^2N)_4 \qquad (1)$$

wherein $R^1$ and $R^2$ each represents a straight-chain or branched alkyl group having 1 to 4 carbon atoms and $R^1$ and $R^2$ may be same or different from each other.

Another implementation of the invention is the material in which the organohafnium compound is Hf $[(C_2H_5)_2N]_4$ (hereinafter, referred to as $Hf(Et_2N)_4$), $Hf[(CH_3)_2N]_4$ (hereinafter, referred to as $Hf(Me_2N)_4$) and $Hf[(CH_3)(C_2H_5)N]_4$ (hereinafter, referred to as $Hf(MeEtN)_4$).

Another implementation of the invention can conveniently form hafnium oxide thin film useful as a gate oxide film when $Hf(Et_2N)_4$, $Hf(Me_2N)_4$ and $Hf(MeEtN)_4$ is used as an organohafnium compound.

Still another implementation of the invention is the material in which the organohafnium compound has a bond of a hafnium atom with an oxygen atom.

Another implementation of the invention is the material in which the organohafnium compound is represented by the following formula 2:

$$Hf(OR^3)_4 \qquad (2)$$

wherein $R^3$ represents a straight-chain or branched alkyl group having 1 to 4 carbon atoms.

Another implementation of the is the material in which the organohafnium compound is Hf $[O(n-C_4H_9)]_4$ (hereinafter, referred to as $Hf(OnBu)_4$), $Hf[O(t-C_4H_9)]_4$ (hereinafter, referred to as $Hf(OtBu)_4$) or $Hf[O(s-C_4H_9)]_4$ (hereinafter, referred to as $Hf(OsBu)_4$) wherein $n-C_4H_9$ is a normal butyl group, $t-C_4H_9$ is a tert-butyl group and $s-C_4H_9$ is a sec-butyl group.

Still another implementation of the invention is the material where an alkali metal element and an alkaline-earth metal element in the material are 1 ppm or less, respectively.

This implementation can provide a highly pure hafnium-containing thin film defining the alkali metal and alkaline-earth metal to being 1 ppm or less, respectively. The alkali metal and alkaline-earth metal can simply move into the gate insulation film and cause deterioration of MOS-LSI interface property.

Another implementation of the invention is the material where the total amount of iron element, zinc element, titanium element, aluminum element, chromium element, and nickel element contained in the material is in the range from 0.1 ppm to 0.8 ppm.

This implementation invention can provide a highly pure Hafnium-containing thin film by defining the total amount of iron, zinc, titanium, aluminum, chromium and nickel in the range of 0.1 ppm to 0.8 ppm. These metals may induce problems on bonded interface portions.

Still another implementation of the invention is the material that further includes an organosilicon compound having a bond of a silicon atom with a nitrogen atom, in addition to the organohafnium compound.

This implementation can form a thin film such as Si—O—Hf thin film by further including the organosilicon compound.

Another implementation of the invention is, as shown in FIG. 1, a method for producing a hafnium-containing material for film formation, including a process for removing impurities contained in an organohafnium compound by means of flash chromatography.

This implementation can provide the hafnium-containing material for film formation with excellent vaporization stability and higher film formation rate by means of the impurity removal process.

Still another implementation of the invention is, as shown in FIG. 3, a method in which the process for removing impurities includes the steps of charging a chelating agent-carrying filler into a pressure-resistant column to form a filler layer inside the column; introducing the organohafnium compound from the upper portion of the filler layer; and adsorbing the impurities contained in the organohafnium compound inside the filler layer, by supplying a predetermined flow rate of pressurized air from the upper portion of the column inside the column to pass the hafnium compound through the filler layer.

This implementation can conveniently reduce the impurities in the organohafnium compound by adsorbing the impurities using the chelating agent-carrying filler.

Another implementation is, as shown in FIG. 2, a method for producing a hafnium-containing material for film formation, including a process for removing impurities contained in a hafnium-containing compound by means of flash chromatography; a process for obtaining a crude product of an organohafnium compound using the hafnium-containing compound and aminolithium; and a reduced-pressure distillation process for distilling the crude product under reduced pressure to obtain the purified product of the compound.

This implementation can provide the hafnium-containing material for film formation with excellent vaporization stability and higher film formation rate through the above processes.

Still another implementation of the invention is a method where a process includes the steps of charging the hafnium-containing compound into a pressure-resistant column to form a filler layer inside the column; adsorbing the impurities contained in the organohafnium compound forming the filler layer to the chelating agent, by introducing a chelating agent from the upper portion of the filler layer to pass the chelating agent through the filler layer; and taking out the hafnium-containing compound forming the filler layer from the column, followed by washing the taken-out hafnium-containing compound with a solvent.

This implementation can conveniently reduce the impurities in the hafnium-containing compound by adsorbing the impurities using the chelating agent.

Another implementation of the invention is a method for producing a hafnium-containing material for film formation, including a process for removing impurities contained in a hafnium-containing compound by means of light irradiation; a process for obtaining a crude product of an organohafnium compound using aminolithium and alcohol together with the hafnium-containing compound; and a reduced-pressure distillation process for distilling the crude product under reduced pressure to obtain the purified product of the compound.

Still another implementation of the invention is a method in which the process for removing the impurities includes the steps of preparing a suspension by suspending the hafnium-containing compound in an ether solution; adding a sintered activated carbon to the suspension; adding zirconium pieces to the suspension, the zirconium pieces being subjected to electrolytic polishing followed by treating the back side thereof with hydrogen peroxide; irradiating the suspension to which the zirconium pieces are added, with visible light or ultraviolet (UV) light; removing the sintered activated carbon and the zirconium pieces from the suspension after irradiation of visible light or UV light; concentrating the suspension to remove an ether component in the suspension; and microfiltrating the concentrated solution after removal of the ether component.

The implementation described above can conveniently reduce the impurities in the hafnium-containing compound by radiating the visible light or the UV light to activate the zirconium pieces and to create photo-response thereof and adsorbing the impurities in the hafnium-containing compound within the zirconium pieces.

Still another implementation of the invention is a hafnium-containing material for film formation, including dissolving in a solvent any of the material described above or any of the material obtained by the method described above.

Still another implementation of the invention is a method for producing a hafnium-containing thin film, including using any of the material described above or any of the material obtained by the method described above by means of Metal Organic Chemical Vapor Deposition.

This invention can provide the hafnium-containing thin film with excellent step coverage by MOCVD process using the above hafnium-containing material.

The hafnium-containing material for film formation and a method for producing the same according to the present invention can inhibit vaporization and pyrolysis characteristics by defining the Zr content to 650 ppm or less, which is generally known to be contained as the inevitable impurity compound in at least 1000 ppm or more among the hafnium material and to inhibit enhancement of film formation rate, thereby obtaining the excellent vaporization stability and the improvement of the film formation rate when using the hafnium-containing material for film formation according to the present invention. Additionally, the hafnium-containing thin film produced using the above material exhibits excellent step coverage. Still further, the process for producing the hafnium-containing thin film can provide the hafnium-containing thin film with excellent step coverage.

DESCRIPTION OF THE PREFERRED EMBODIMENTS

Figure 1:
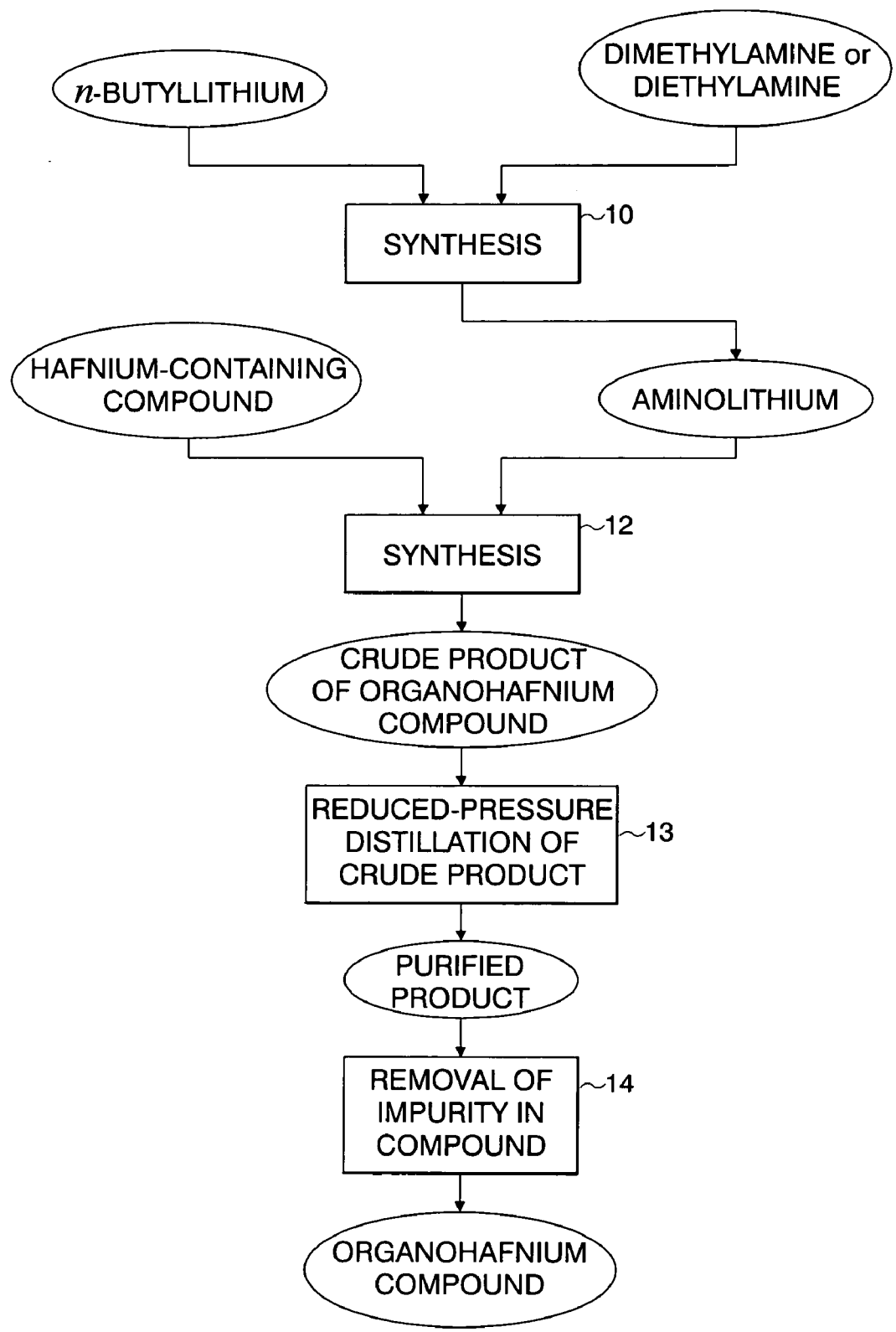
FIG. 1 is a flow chart illustrating the first method for producing a hafnium-containing material for film formation according to the present invention.

The preferred embodiments of the present invention will be described hereinafter with reference to the drawings.

A hafnium-containing material useful for forming a film according to the present invention is an enhancement over typically known materials including organohafnium compound, which was applied to formation of the hafnium-containing film. The present material is characterized in that it contains 650 ppm or less of zirconium element therein. Since the inventive material can control vaporization and pyrolysis characteristics by defining the content of the zirconium element as an obstacle of increase of film formation rate, to 650 ppm or less, preferably 500 ppm or less, thereby resulting in excellent vaporization stability and improved film formation rate in production of the hafnium-containing film. The content of the zirconium element in the material preferably ranges from 50 to 100 ppm. When the material contains the zirconium element in the range of 50 to 100 ppm, it is possible to improve close adhesion ability of a film formed using the material to a substrate. If the Zr content in the material is less than 50 ppm, it has a difficulty in the film formation. The organohafnium compound has preferably bonds of hafnium atoms with nitrogen atoms. Particularly, it is desirable that the organohafnium compound is represented by the following formula 1:

$$Hf(R^1R^2N)_4 \quad (1)$$

wherein $R^1$ and $R^2$ each represents a straight-chain or branched alkyl group having 1 to 4 carbon atoms and $R^1$ and $R^2$ may be same or different from each other.

Example of an alkyl group for $R^1$ and $R^2$ includes, but is not limited to, methyl, ethyl, propyl and butyl. Among them, any one selected from $Hf(Et_2N)_4$, $Hf(Me_2N)_4$ or $Hf(MeEtN)_4$ is more preferably applied in preparation of a gate oxide film.

Alternatively, the organohafnium compound has preferably a bond of a hafnium atom with a nitrogen atom. Particularly, it is desirable that the organohafnium compound is represented by the following formula 2.

$$Hf(OR^3)_4 \quad (2)$$

wherein $R^3$ represents a straight-chain or branched alkyl group having 1 to 4 carbon atoms.

Example of an alkyl group for $R^3$ include, but is not limited to, methyl, ethyl, propyl and butyl. Among them, any one selected from $Hf(OnBu)_4$, $Hf(OtBu)_4$ or $Hf(OsBu)_4$ is more preferably applied in preparation of a gate oxide film.

$Hf(OR^3)_4$ with the Zr content reduced at most to the range defined above can form the film at low temperature and exhibit improved reproducibility.

Next, it will be described in detail about a first method for preparing the organohafnium compound with the defined Zr content of 650 ppm or less as the hafnium-containing material for film formation according to the present invention with reference to $Hf(Et_2N)_4$ as an illustrative example.

First, as shown in FIG. 1, aminolithium is obtained by carrying out a reaction of n-butyllithium with diethylamine (Process 10). The reaction of n-butyllithium and diethylamine is represented by the following reaction scheme 3:

$$Li(CH_2)_3CH_3 + (C_2H_5)_2NH \rightarrow (C_2H_5)_2NLi + CH_3(CH_2)_2CH_3 \quad (3)$$
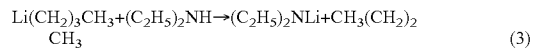

Next, to a hafnium-containing compound, added is aminolithium in an amount of moles corresponding to times of atomic value number of the hafnium-containing compound to lead reaction between them to obtain a crude product of the organohafnium compound (Process 12). The hafnium-containing compound includes, but is not limited to, hafnium tetrachloride (HfCl$_4$), hafnium halide, hafnium diethylamide, nitrogen-containing hafnium, etc. The reaction according to the process 12 takes about 30 minutes and is accelerating by continuously retaining the reaction under ice-cooling. The reaction can be illustrated by the following reaction scheme 4 in case of using HfCl$_4$ as the hafnium-containing compound as well as (C$_2$H$_5$)$_2$NLi as the aminolithium. Also, Hf[(C$_2$H$_5$)$_2$N$_4$] in the scheme 4 is the same as the compound represented by Hf(Et$_2$N)$_4$.

$$HfCl_4 + 4(C_2H_5)_2NLi \rightarrow Hf[(C_2H_5)_2N_4] + 4LiCl\downarrow \qquad (4)$$

When the hafnium-containing compound is HfCl$_4$, it provides a crude product of Hf(Me$_2$N)$_4$ with the aminolithium of (CH$_3$)$_2$NLi, while the crude product of Hf(Et$_2$N)$_4$ is obtained in case of (C$_2$H$_5$)$_2$NLi for the aminolithium.

Then, the obtained crude product is left at room temperature then taken by a distillation process under a condition of vacuum pressure to result in a purified product (Process 13). In this process, most of LiCl is eliminated by means of vacuum-distillation and purification under a condition of, for example, about 100° C. and 3.99 kPa (30 Torr) of pressure for one or two or more times. The resultant product through the process 13 normally includes Zr element in a range of about 700 to 1000 ppm, alkali metal and alkaline-earth metal elements in a range of about 2 to 10 ppm, and iron, zinc, titanium, aluminum, chromium and nickel elements totally in a range of about 10 to 50 ppm as necessary impurities. If Zr as one of the necessary impurities is contained in the hafnium-containing material useful for film formation in any compounding ratio within the above range, the product has poor volatility and decrease of film formation rate, or causes deterioration of step coverage for hafnium-containing thin film produced using the inventive hafnium-containing material. Moreover, if each of the alkali metal and alkaline-earth metal elements is included in the hafnium-containing material in any compounding ratio within the above range, such elements can easily move into a gate insulation film which was manufactured using the above film forming material and become a cause to induce deterioration of MOS-LSI interface property of the gate insulation film. In addition, when the hafnium-containing material further comprises all of iron, zinc, titanium, aluminum, chromium and nickel elements in any compounding ratio within the above range, such elements may be concerned a trouble in interface bonding portion of the gate insulation film which was manufactured using such material.

The method for preparation of the material useful for forming the hafnium-containing film according to the present invention is characterized in that it comprises a process for removal of impurities 14 to exclude the impurities in the organohafnium compound by means of flash chromatography. By this removal process 14, obtained is the hafnium-containing material for film formation with excellent vaporization stability and higher film formation rate. Representative example of the impurities capable of being eliminated from the organohafnium compound by the removal process 14 comprises Zr but is not limited thereto. Further, example of the impurities removed out of the organohafnium compound comprises alkali metal or alkaline-earth metal elements. Still further, as the impurities in the organohafnium compound to be removed, iron, zinc, titanium, aluminum, chromium or nickel elements may be also exemplified.

Figure 3:
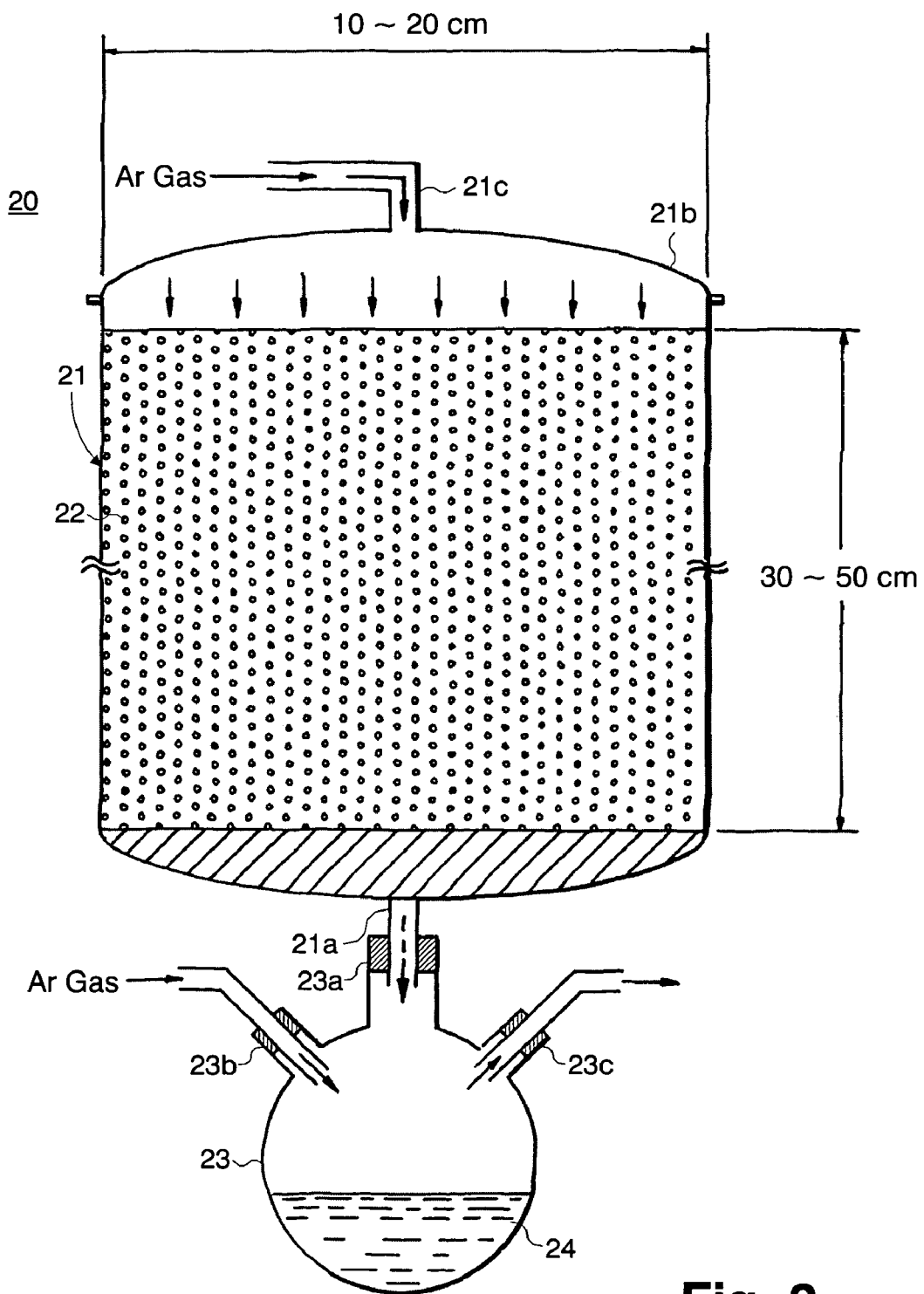
FIG. 3 is a schematic explanatory view of a flash chromatography apparatus.

Such impurity removal process 14, as shown in FIG. 3, is proceeding using a flash-chromatographic apparatus 20. This apparatus 20 comprises a pressure-resistant column 21 equipped with an outlet 21a on lower portion thereof, and an Erlenmeyer flask 23 having an opening 23a on the center of the flask to be connected to the outlet 21a. The column 21 is preferably a pressure-resistant column made of glass material and having a diameter ranging from 10 cm to 20 cm and a height ranging from 30 cm to 50 cm. On upper portion of the column 21, a top cover 21b is provided and a gas-inlet 21c is mounted on top of the cover 21b. First, a chelating agent-carrying filler is charged into the pressure-resistant column 21 to form a filler layer 22 inside the column.

As the chelating agent, exemplified is EDTA (ethylenediamine tetraacetate), EDTA disodium hydrate, EDTA trisodium hydrate, EDTA tetrasodium hydrate, EDTA dipotassium hydrate, EDTA tripotassium hydrate, EDTA diammonium hydrate, BAPTA (bis(aminophenyl)ethyleneglycol tetrapotassium hydrate tetraacetate), bicin, CyDTA (cyclohexane diamine tetraacetate), DTPA (diethylenetriamine pentaacetate), EDDP (ethylenediamine acid dihydrochloride dipropionate), EDTA-OH (hydroxyethylenediamine triacetate), GEDTA (glycoletherdiamine tetraacetate), HIDA (hydroxyethylimino diacetate), IDA (imino diacetate), NTA (nitrilo triacetate), NTPO (nitrilo trismethylene phosphonate trisodium), TPEN (tetrakis(pyridylmethyl)ethylenediamine), TTHA (triethylene tetramine hexaacetate), BFA (trifluorophenylbutanedione), DPM (tetramethylheptanedione), HFA (hexanefluoropentanedione), TOPO (trioctylphosphine oxide), TTA (trifluorothienylbutanedione), etc.

The filler for column is not particularly limited to any material as far as it is in the granular form carrying the chelating agent, but preferably comprises any one or two or more selected from a group consisting of SiO$_2$, Al$_2$O$_3$, ZrO$_2$, TiO$_2$ and HfO$_2$ particles having a mean diameter ranging from 0.3 µm to 0.5 µm, and a particle size distribution d$_{90}$/d$_{10}$ ranging from 0.8 to 1.2. More preferably is Al$_2$O$_3$ particles having a mean diameter ranging from 0.4 µm to 0.45 µm and a particle size distribution d$_{90}$/d$_{10}$ ranging from 0.90 to 1.0. Specifically, 500 g to 1000 g of the chelating agent-carrying filler is charged into the column to form the filler layer 22. Into the Erlenmeyer flask 23, is poured Ar gas from one side 23b of the opening portion followed by the Ar gas being exhausted through the other side 23c of the opening portion, thereby keeping inside of the flask 23 to be charged with inert-gas atmosphere.

The apparatus 20 having such construction described above is operated by opening the top cover 21b of the column 21 and pouring the purified product of the organohafnium compound obtained through the process 13 from upper portion of the filler layer 22. Amount of the purified product entered is varied depending on volume of the filler layer 22 but preferably ranges from 200 ml to 300 ml when the filler layer 22 is formed, for example, with a height ranging from 15 cm to 20 cm in the column having a diameter ranging from 15 cm to 20 cm and a height ranging from 40 cm to 45 cm.

For example, in case of EDTA being applied as the chelating agent to form the filler layer 22, Hf element in Hf(Et$_2$N)$_4$ will be adsorbed to carboxylic group in EDTA by a specified reaction scheme 5 when Hf(Et$_2$N)$_4$ is introduced into the filler layer 22. Herein, EDTA is partially illustrated to represent absorbed portion with the Hf element in the following formula 5:

(5)

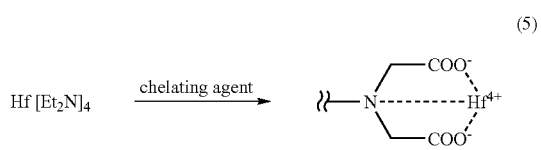

Next, the top cover 21b of the column 21 is closed to receive a predetermined flow rate of pressurized gas into the column 21 through the gas-inlet 21c at top of the cover 21b. This pressurized gas is for transferring the purified product into the filler layer 22. During the purified product passes through the filler layer 22, the impurities in the purified product is typically adsorbed to the filler. The pressurized gas includes Ar gas but is not limited thereto. The purified product passes through the filler layer 22 so that gaseous pressure of such gas is defined to a range of 1 kg to 2 kg and a column flow rate thereof as the space velocity value (SV value) is determined to 2 to 4 cm/min.

By passing the purified product through the filler layer 22, Zr as one of the impurities is exchanged by Hf element already adsorbed to the carboxyl group in the chelating agent, EDTA, thus entrapped to EDTA based on the following reaction scheme 6. Hf element free out of EDTA forms Hf(Et$_2$N)$_4$. Via such reaction, removed is Zr in Hf (Et$_2$N)$_4$.

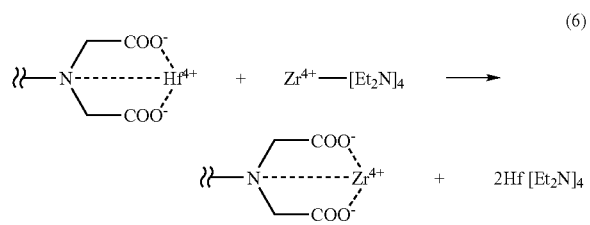

The impurity removal process 14 eliminates Zr element out of the purified product. Similarly, alkali metal or alkaline-earth metal elements, as well as other impurities such as iron, zinc, titanium, aluminum, chromium or nickel elements are removed from the purified product. Such removal of impurities including Zr element; alkali metal or alkaline-earth metal elements; and others such as iron, zinc, titanium, aluminum, chromium or nickel elements by the impurity removal process 14 is under a principle of coordination effect of metals. As a result, the obtained organohafnium compound has the Zr content of 650 ppm or less. From the above processes, the present invention provides the hafnium-containing material useful for film formation, which includes Hf(Et$_2$N)$_4$ with the limited Zr content of 650 ppm or less. Further, amounts of the alkali metal element and alkaline-earth metal element, respectively, become 1 ppm in the organohafnium compound. Still further, total amount of other impurities including iron, zinc, titanium, aluminum, chromium and nickel elements become the range of 0.1 ppm to 0.8 ppm.

Next, it will be described in detail about a second method for preparing the organohafnium compound with the defined Zr content of 650 ppm or less as the hafnium-containing material according to the present invention useful for film formation with reference to Hf(Me$_2$N)$_4$ as another illustrative example.

Figure 2:
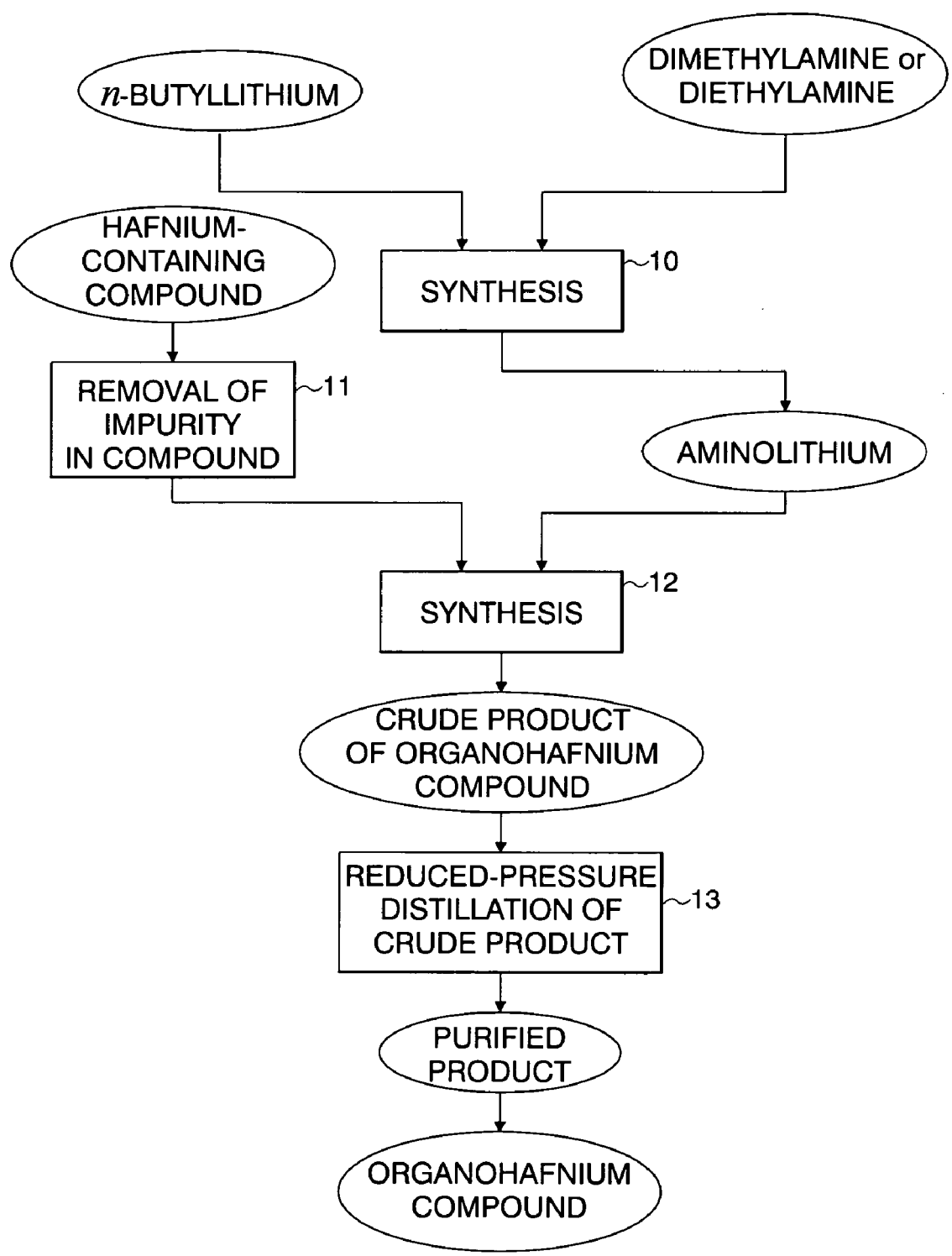
FIG. 2 is a flow chart illustrating the second method for producing a hafnium-containing material for film formation according to the present invention.

First, as shown in FIG. 2, aminolithium is obtained by carrying out a reaction of n-butyllithium with dimethylamine (Process 10). The reaction of n-butyllithium and dimethylamine is represented by the following formula 7

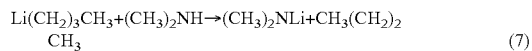

$$Li(CH_2)_3CH_3+(CH_3)_2NH \rightarrow (CH_3)_2NLi+CH_3(CH_2)_2CH_3 \quad (7)$$

Next, impurities in the hafnium-containing 14 is removed by means of flash chromatography (Process 11). The hafnium-containing compound includes, but is not limited to, hafnium tetrachloride HfCl$_4$, hafnium halide, hafnium diethylamide, nitrogen-containing hafnium, etc. Representative example of the impurities capable of being eliminated from the organohafnium compound by such removal process 11 comprises Zr but is not limited thereto. Further, example of the impurities removed out of the organohafnium compound comprises alkali metal or alkaline-earth metal elements. Still further, as the impurities in the organohafnium compound to be removed, iron, zinc, titanium, aluminum, chromium or nickel elements may be also exemplified.

Such impurity removal process 11 is processing using an apparatus with a structure same to the flash chromatography apparatus 20 as shown in FIG. 3. Firstly, a hafnium-containing compound is charged into the pressure-resistant column 21 to form a filler layer 22 inside the column 21. The hafnium-containing compound used in the present invention is prepared in the powder form to construct the filler layer 22 inside the column.

Next, a constant amount of the chelating agent is poured from upper portion of the filler layer 22 over a constant time period. The chelating agent is preferably same to those already illustrated for the first method above. Such chelating agent poured passes through the filler layer 22 and adsorbs the impurities in the hafnium-containing compound forming the filler layer 22. After introduction of the chelating agent into the column 21, the chelating agent naturally flows down and passes through the filler layer 22.

Then, the hafnium-containing compound forming the filler layer 22 is taken out of the column then rinsed by any corresponding solvent. After passing the chelating agent through the filler layer 22, the outlet 21a mounted on lower portion of the column 21 is closed and the hafnium-containing compound is taken out of inside the column, for example, under reduced pressure. The obtained hafnium-containing compound is washed with a solvent such as hexane or toluene. During washing the compound, the impurities such as Zr element is released from the hafnium-containing compound then eluted into the solvent.

Subsequently, the obtained hafnium-containing compound is under filtration to reduce the Zr content of the compound at most up to 650 ppm or less. Further, amounts of the alkali metal element and alkaline-earth metal element, respectively, become 1 ppm or less in the hafnium-containing compound. Still further, total amount of other impurities including iron, zinc, titanium, aluminum, chromium and nickel elements becomes the range of 0.1 ppm to 0.8 ppm.

Next, to a hafnium-containing compound after removal of the impurities, added is aminolithium in an amount of moles corresponding to times of atomic value number of the hafnium-containing compound to lead reaction between them to obtain a crude product of the organohafnium compound (Process 12). The reaction according to the process 12 takes about 30 minutes and is accelerating by continuously retaining the reaction under ice-cooling. The reaction can be illustrated by the following reaction scheme 8 in case of using HfCl$_4$ as the hafnium-containing compound as well as $(CH_3)_2NLi$ as the aminolithium. Also, $Hf[(CH_3)_2N]_4$ in the formula 8 is same to the compound represented by $Hf(Me_2N)_4$.

 (8)

Next, the obtained crude product is left at room temperature then taken by a distillation process under a condition of vacuum pressure to result in the purified product (Process 13). In this process, most of LiCl is eliminated by means of vacuum-distillation and purification under the condition of, for example, about 100° C. and 3.99 kPa (30 Torr) of pressure for one or two or more times. The resultant hafnium-containing compound normally includes Zr element in a range of 650 ppm or less. Additionally, alkali metal element and alkaline-earth metal element, respectively, become 1 ppm or less, while total amount of iron, zinc, titanium, aluminum, chromium and nickel elements being in a range of about 0.1 ppm to 0.8 ppm. From the above processes, the present invention provides the material useful for forming the hafnium-containing film which includes $Hf(Me_2N)_4$ with the limited Zr content of 650 ppm or less.

Moreover, it will be described in detail about a further method for preparing the hafnium-containing material useful for film formation as follows:

First, it is prepared a hafnium tetrachloride product available in market. This product includes Zr content ranging from about 700 ppm to 1000 ppm, and thus, it is well known to very difficult to reduce the Zr content therefrom. And, a suspension is formed by preparing toluene as the solvent, adding and suspending hafnium tetrachloride in the solvent. And, 3-chloro-hexafluoroacetylacetone and 3-chloro-2,4-pentanedione are prepared, respectively. These compound are blended together in a relative combination ratio of 1:10 by weight, followed by diluting the blend with diethyl ether as a solvent to form a diluted solution in which the solvent takes 80% of total composition in the solution the suspension and the diluted solution together are mixed to produce a reaction solution of hafnium tetrachloride.

Subsequently, to alkali metal such as metallic lithium or metallic sodium, metallic potassium, added is toluene as the solvent followed by heating to 50° C. to lead the reaction. The obtained supernatant reaction solution is gradually added dropwise to the hafnium tetrachloride reaction solution under ice-cooling. Thereafter, the precipitate is removed by filtrating the hafnium tetrachloride reaction solution after adding dropwise the supernatant reaction solution. The filtrate is slowly added with 0.1 N dilute hydrochloric acid while cooling the solution. White solids precipitated by adding the dilute hydrochloric acid is rapidly separated, followed by the separation of oil and aqueous phases. The filtrated white solids contain the zirconium element.

Further, the separated aqueous phase is under extraction of components therein by adding ligroin. The extraction is repeatedly conducted for about 10 times or more. Finally, to the extracts, anhydrous sodium sulfate is added then leaves for about 24 hours to be dried. By such processes, removal of Zr component is accomplished by means of chemical extraction.

Next, radiation of UV light having about 365 nm wavelength is applied for about 1 hour to the ligroin extracts. Such UV light irradiation is conducted using a mercury lamp. The extracts after the UV light irradiation is added with diethylamine in an amount equal to four (4) times of moles, followed by further UV light irradiation over 2 hours. Herein, thermal decomposition by diketone absorption of a chelating compound produced of precursor causes new amino bonds formed, in turn, amine and hafnium reactions. Termination of the thermal decomposition is proceeding while tracing spectrum analysis of UV light absorption type spectroscopy and, continued until absorption of the diketone precursor (310 nm, charge-transferring transition bandwidth) is disappeared, while novel bandwidth for the hafnium amine compound (380 to 400 nm, d-d transition) is appeared. It takes about 2 hours for the inner radiation synthesis. By conducting the above method with improved accuracy (solvent extraction frequency, selection of solvent, etc.), it can accomplish reduction of Zr content in the obtained $Hf(Et_2N)_4$ to 650 ppm or less and synthesis of purposed material by means of photo-response.

Additionally, the above method used 3-chloro-hexafluoroacetylacetone and 3-chloro-2,4-pentanedione, but other similar chlorides chelate derivatives may also be applied to prepare the diluted solution.

Furthermore, it will be described in detail about another method for preparing the hafnium-containing material for film formation as follows:

First, it is prepared the hafnium tetrachloride available in market which includes 1000 ppm or more of Zr element and absolute ether as an organic catalyst. Then, the hafnium tetrachloride is suspended in the absolute ether to form a suspension. Also, respectively prepared are a sintered activated carbon in the spherical shape and zirconium pieces obtained after electrolytic polishing, back-side treatment with hydrogen peroxide. Such a sintered activated carbon can inhibit hydrolysis or the like effected to the hafnium-containing compound. Because surface of the zirconium piece is activated by the electrolytic polishing, the back-side treatment with hydrogen peroxide, the photoreaction following the above treatment to the zirconium piece is accelerating. Then, after adding the spherical shape a sintered activated carbon, the suspension is under stirring at room temperature. The stirring time is preferably 18 to 24 hours. Next, the zirconium piece is entered in the suspension containing the activated carbon followed by light irradiation of visible light and/or UV light to the suspension to generate photo-response thereto. The frequency bandwidth preferably ranges from 271 to 450 nm. Depending on size or area of the zirconium piece introduced in the suspension, condition of surface treatment, etc. time of the light irradiation is varied, however, the longer the light irradiation time period the more the amount of zirconium in the hafnium-containing compound is reduced. Preferably, the time for light irradiation ranges from 30 minutes to 1 hour. After the light irradiation, the a sintered activated carbon and the zirconium piece are filtrated out of the suspension and the residual suspension is concentrated to remove ether component, followed by microfiltration through porous filter having fine pores, etc. to result in a purified product of hafnium tetrachloride. Further, to the purified hafnium tetrachloride product, alkyllithium and alcohol are added to cause reaction between them in a stoichiometric ratio in the presence of an organic solvent such as tetrahydrofuran. As a result, obtained is an organohafnium compound having bonds of hafnium atoms and oxygen atoms. The present hafnium-containing material useful for film formation comprising the above resultant organohafnium compound with the reduced zirconium content and the hafnium-oxygen atom bonds can form the film at low temperature and exhibit excellent reproducibility.

Each of the alkali metal element and the alkaline-earth metal element preferably in the film forming material has the content of about 1 ppm or less. When the alkali metal and alkaline-earth metal elements which may cause deterioration of MOS-LSI interface property have the content limited to 1 ppm or less, obtained is the higher purity hafnium-containing thin film. In addition, it is preferable to define the content of each of elements such as iron, zinc, titanium, aluminum, chromium and nickel to 0.1 ppm to 0.8 ppm. By limiting the content to the above range for such element which may be a trouble in interface bonding portion of the gate insulation film, obtained is the higher purity hafnium thin film.

The material according to the invention can form the thin film such as Si—O—Hf thin film by further comprising the organosilicon compound having bonds of silicon atoms and nitrogen atoms, in addition to the organohafnium compound. In this case, the compounding ratio between the organosilicon compound and the organohafnium compound typically ranges from 2:1 to 10:1, preferably 8:1 by weight of organosilicon compound to organohafnium compound. If the weight ratio is less than 2:1 or exceeds 10:1, Si—O—Hf thin film with desirable composition is not obtainable for neither of the cases.

Preferable organosilicon compound in the present invention is represented by the following formula 9:

$$(R^4R^5N)_n SiH_{n-4} \quad (9)$$

wherein $R^4$ and $R^5$ each represents a straight-chain or branched alkyl group having 1 to 4 carbon atoms and $R^4$ and $R^5$ may be same or different from each other, and n is an integer of 1 to 4.

Example of an alkyl group for $R^4$ and $R^5$ includes, but is not limited to, methyl, ethyl, propyl and butyl. The organosilicon compound of the above formula 9 comprises, but is not limited to, any one selected from $(Et_2N)_4Si$, $(Et_2N)_3SiH$, $(Et_2N)_2SiH_2$, $(Me_2N)_4Si$, $(Me_2N)_3SiH$, and $(Me_2N)_2SiH_2$.

Further, the organosilicon compound may represented by the following formula 10:

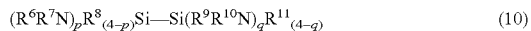

$$(R^6R^7N)_p R^8_{(4-p)} Si-Si(R^9R^{10}N)_q R^{11}_{(4-q)} \quad (10)$$

wherein $R^6$, $R^7$, $R^9$ and $R^{10}$ each represents a straight-chain or branched alkyl group having 1 to 4 carbon atoms and $R^6$, $R^7$, $R^9$ and $R^{10}$ may be same or different from one another, $R^8$ and $R^{11}$ each represents hydrogen, or a straight-chain or branched alkyl group having 1 to 4 carbon atoms and p is an integer of 1 to 4.

Example of an alkyl group for $R^6$, $R^7$, $R^9$ and $R^{10}$ includes, but is not limited to, methyl, ethyl, propyl, and butyl. Example of an alkyl group for $R^8$ and $R^{11}$ also includes methyl, ethyl, propyl, and butyl, but is not limited thereto. The organosilicon compound of the above formula 10 comprises, but is not limited to, any one selected from $[(Et_2N)_2HSi-]_2$, $[(Et_2N)_2MeSi-]_2$, $[(Me_2N)_2HSi-]_2$ and $[(Me_2N)_2MeSi-]_2$.

The hafnium-containing film forming material according to the present invention is preferably dissolved in any corresponding solvent in a predeterminded proportion to form a solution. As the corresponding solvent, exemplified is any one or two or more selected from a group consisting of hydrocarbon compounds having 6 to 10 carbon atoms and amine compounds having 2 to 6 carbon atoms. The hydrocarbon compounds having 6 to 10 carbon atoms comprise hexane, octane and decane but are not limited thereto, while the amine compounds having 2 to 6 carbon atoms include dimethylamine, diethylamine and dipropylamine but are not limited thereto.

The hafnium-containing thin film according to the present invention is prepared by means of chemical vapor deposition process using the hafnium-containing material useful for forming the film. Hereinafter, it will be described in detail for a process for forming a hafnium oxide thin film by MOCVD process using the hafnium-containing material according to the present invention.

Figure 5:
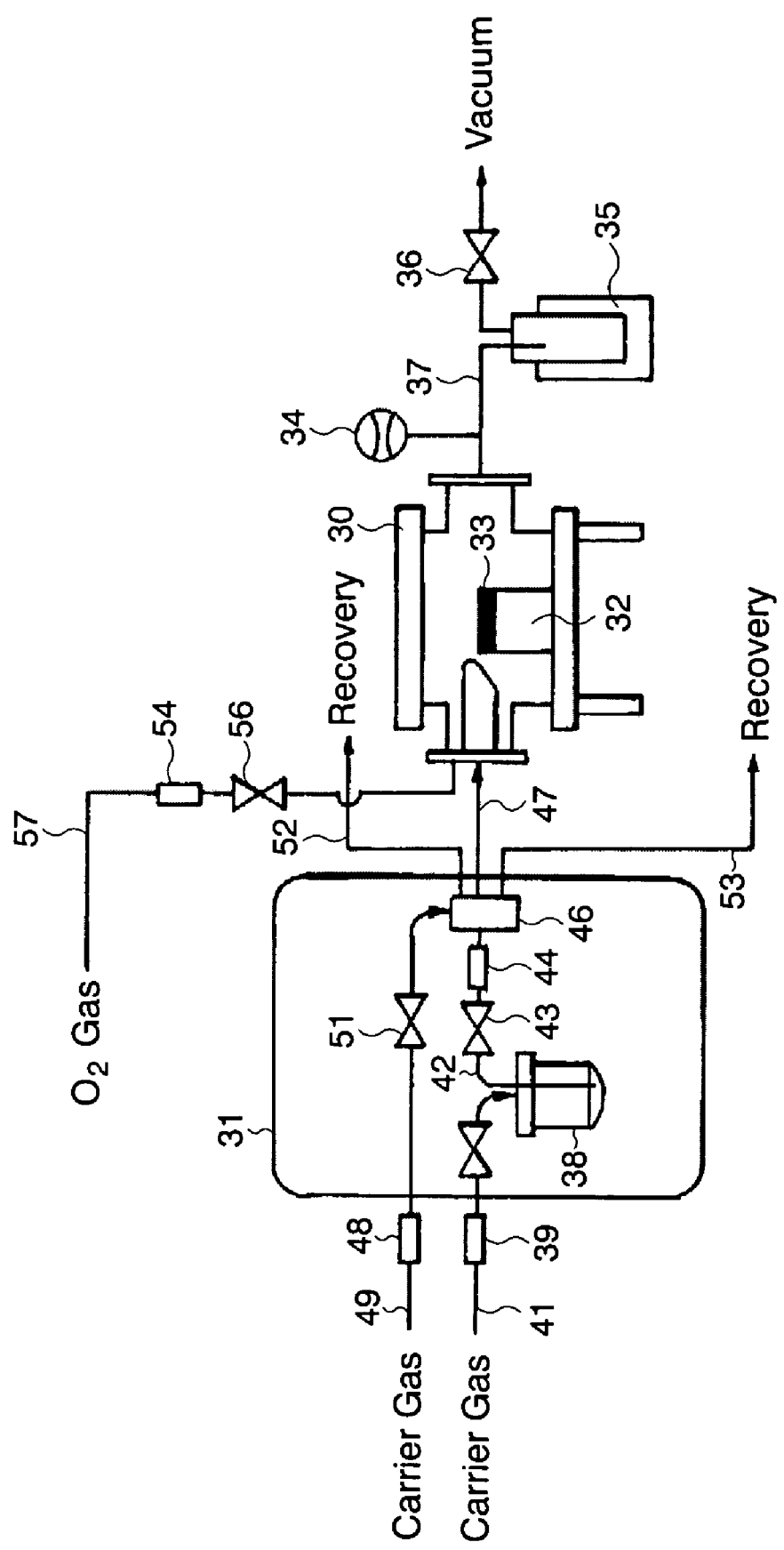
FIG. 5 is a schematic view of MOCVD apparatus.

As shown in FIG. 5, a MOCVD apparatus comprises a film formation chamber 30 and a steam generator 31. Inside the film formation chamber 30, equipped is a heater 32 having an engine 33. Inner space of the chamber 30 is maintained under vacuum condition by means of a piping 37 mounted with a pressure sensor 34, a cold trap 35 and a needle valve 36. The chamber 30 is connected to $O_2$ gas introduction pipe 57 through the needle valve 36 and a gas flow rate control device 54. On the steam generator 31, mounted is a material-supplying container 38 to store the hafnium-containing material for film formation according to the present invention. With regard to an embodiment of the present invention, a material solution comprising the organohafnium compound containing 650 ppm or less of Zr dissolved in a desirable solvent is applied as the hafnium-containing material for film formation. The supply container 38 is connected to an inert-gas introduction pipe 41 for pressurizing via another gas flow rate control device 39 and a supply pipe 42. To the supply pipe 42, mounted are another needle valve 43 and a flow rate control device 44. The supply pipe 42 is further connected to a vaporization chamber 46. Via the needle valve 51 and the gas flow rate control device 48, a carrier gas introduction pipe 49 is connected to the vaporization chamber 46. The vaporization chamber 46 is also connected to a film formation chamber 30 by means of the piping 47. Further, a gas-drain 52 and a drain 53 are connected to the vaporization chamber 46, respectively.

According to the present apparatus, the pressurizing inert gas out of the gas introduction pipe 41 is introduced into the material-supplying container 38 and the solution material stored in the container 38 is returned through the supply pipe 42 into the vaporization chamber 46. The organohafnium compound transferred into vapor state within the vaporization chamber 46 is supplied into the film formation chamber 30 via the piping 47 by the carrier gas out of the gas introduction pipe 49 introduced into the vaporization chamber 46. Within the film formation chamber 30, the organohafnium compound in the vapor state is thermally decomposed (that is, under pyrolysis) then under reaction with $O_2$ gas introduced from the $O_2$ gas introduction pipe 57 to generate a hafnium oxide product, followed by deposition of the product on a substrate 33 to result in a hafnium oxide thin film. As the pressurizing inert-gas and the carrier gas, preferably exemplified is argon, helium, nitrogen or the like.

As described above, when the hafnium-containing material useful for forming the film according to the present invention which has a higher film formation rate is applied in production of the film, it is possible to form the film with improved film formation rate, compared to conventional hafnium-containing materials useful in film formation, thereby obtaining the hafnium-containing thin film having excellent step coverage.

EXAMPLES

Examples of the present invention will be described in detailed with Comparative Examples.

Example 1

Hafnium tetrachloride containing 1000 ppm or more of Zr element, which is commercially available, and toluene were prepared. Also, a suspension was prepared by suspending the hafnium tetrachloride in the toluene. Further, 3-chloro-hexafluoroacetylacetone and 3-chloro-2,4-pentanedione were prepared, respectively and mixed in a weight ratio of 1:10. The obtained mixture was dissolved in diethyl ether as a solvent to form a diluted solution, in which the solvent takes 80% of total weight of the solution. The suspension and the diluted solution were mixed to produce a reaction solution of hafnium tetrachloride.

Subsequently, to an alkali metal such as metallic lithium or metallic sodium, metallic potassium was added toluene as the solvent followed by heating to 50° C. to react. The obtained supernatant reaction solution was gradually added dropwise to the hafnium tetrachloride reaction solution under ice-cooling. Thereafter, the precipitate was removed by filtrating the hafnium tetrachloride reaction solution after adding dropwise the supernatant reaction solution. To the filtrate was gradually added 0.1 N dilute hydrochloric acid while cooling the solution. White solids precipitated by adding the dilute hydrochloric acid were rapidly separated by filtration, followed by the separation of oil and aqueous phases.

Furthermore, ligroin was added to the separated aqueous phase to extract components therein. The extraction was 10 times repeated. Finally, to the extracts was added anhydrous sodium sulfate and then left for about 24 hours to be dried.

Furthermore, irradiation of UV light having about 365 nm wavelength was applied for about 1 hour to the ligroin extracts. To the extracts after the UV light irradiation was added diethylamine in an amount of 4 times mole equivalents, followed by further UV light irradiation over 2 hours for reacting the amine with the hafnium. Thus, $Hf(Et_2N)_4$ was obtained. As a result of determination of Zr content in the obtained $Hf(Et_2N)_4$ by means of UV-VIS (UV-Visible Spectroscopy) absorption spectrum analysis, the Zr content was 500 ppm. The resultant $Hf(Et_2N)_4$ having 500 ppm of the Zr content was used as the hafnium-containing material for film formation.

Example 2

$Hf(Et_2N)_4$ was prepared in the same manner as in Example 1, except that the ligroin extraction was repeated for 15 times. As a result of determination of the Zr content in the obtained $Hf(Et_2N)_4$ by means of UV-VIS absorption spectrum analysis, the Zr content was 100 ppm. The resultant $Hf(Et_2N)_4$ having 100 ppm of the Zr content was used as the hafnium-containing material for film formation.

Example 3

$Hf(Et_2N)_4$ was prepared in the same manner as in Example 1, except that the ligroin extraction was 18 times repeated. As a result of determination of the Zr content in the obtained $Hf(Et_2N)_4$ by means of UV-VIS absorption spectrum analysis, the Zr content was 50 ppm. The resultant $Hf(Et_2N)_4$ having 50 ppm of Zr content was used as the hafnium-containing material for film formation.

Example 4

$Hf(Et_2N)_4$ was prepared in the same manner as in Example 1, except that the ligroin extraction was 22 times repeated. As a result of determination of the Zr content in the obtained $Hf(Et_2N)_4$ by means of UV-VIS absorption spectrum analysis, the Zr content was 10 ppm. The resultant $Hf(Et_2N)_4$ having 10 ppm of Zr content was used as the hafnium-containing material for film formation.

Example 5

$Hf(Et_2N)_4$ was prepared in the same manner as in Example 1, except that the ligroin extraction was 30 times repeated. As a result of determination of the Zr content in the obtained $Hf(Et_2N)_4$ by means of UV-VIS absorption spectrum analysis, the Zr content was 5 ppm. The resultant $Hf(Et_2N)_4$ having 5 ppm of Zr content was used as the hafnium-containing material for film formation.

Example 6

$Hf(Et_2N)_4$ was prepared in the same manner as in Example 1, except that the ligroin extraction was 35 times repeated. As a result of determination of the Zr content in the obtained $Hf(Et_2N)_4$ by means of UV-VIS absorption spectrum analysis, the Zr content was less than 5 ppm. The resultant $Hf(Et_2N)_4$ having less than 5 ppm of Zr content was used as the hafnium-containing material for film formation.

Example 7

$Hf(Et_2N)_4$ was prepared in the same manner as in Example 1, except that hafnium tetrachloride which is commercially available and contains 1500 ppm or more of Zr element was used. As a result of determination of the Zr content in the obtained $Hf(Et_2N)_4$ by means of UV-VIS absorption spectrum analysis, the Zr content was 650 ppm. The resultant $Hf(Et_2N)_4$ having 650 ppm of Zr content was used as the hafnium-containing material for film formation.

Comparative Example 1

First, diethylaminolithium was synthesized from n-butyllithium and diethylamine. Next, a crude product was obtained by using $HfCl_4$ containing 20000 ppm or more of Zr element, adding to the above $HfCl_4$ the obtained diethylaminolithium in an amount of 4 times moles to form a solution and reacting the solution for 30 minutes under ice-cooling. Then, after returning the crude product to room temperature, a purified product of $Hf(Et_2N)_4$ was obtained by carrying out distillation and purification of the crude product under reduced pressure at 100° C. and 3.99 kPa (30 Torr). As a result of determination of the Zr content in the obtained $Hf(Et_2N)_4$ by means of UV-VIS absorption spectrum analysis, the Zr content exceeded 1000 ppm. The resultant $Hf(Et_2N)_4$ having more than 1000 ppm of Zr content was used as the hafnium-containing material for film formation.

Comparative Example 2

$Hf(Et_2N)_4$ was prepared in the same manner as in Example 1, except that the ligroin extraction was 5 times repeated. As a result of determination of the Zr content in the obtained $Hf(Et_2N)_4$ by means of UV-VIS absorption spectrum analysis, the Zr content was 700 ppm. The resultant $Hf(Et_2N)_4$ having 700 ppm of Zr content was used as the hafnium-containing material for film formation.

Comparative Evaluation 1

For each of the hafnium-containing materials obtained in Examples 1, 2 and 4, and Comparative Examples 1 and 2, performed was thermal weight determination under a condition where a temperature elevation rate is 10° C./min and a measurement temperature ranges from room temperature to 500° C. The obtained TG curves for respective cases were shown in FIG. 4.

Figure 4:
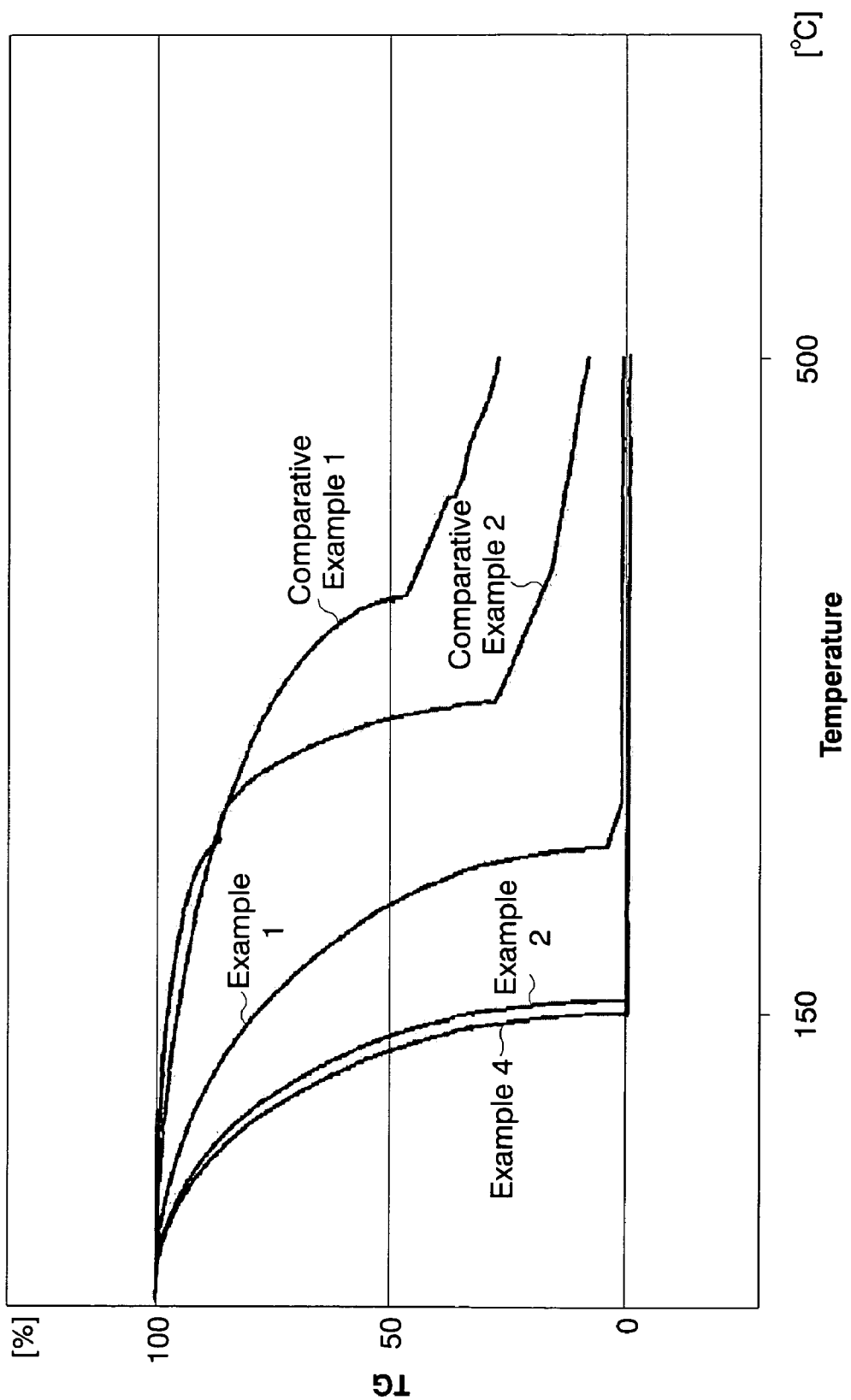
FIG. 4 shows TG curves for hafnium-containing materials obtained as in Examples 1, 2 and 4, and Comparative Examples 1 and 2.

As clearly illustrated in FIG. 4, it was understood that the Zr content in the organohafnium compound has a great influence on volatility of the organohafnium compound. In Comparative Examples 1 and 2, volatilization was not sufficient, and thus resulted in 25% by weight of the black residues for Comparative Example 1 while 12% by weight for Comparative Example 2. In contrast, in Examples 1, 2 and 4, the volatility was improved, and thus resulting in the more excellent volatility with the reduced Zr content.

Comparative Evaluation 2

By using each of the hafnium-containing materials obtained in Examples 1 to 7, and Comparative Examples 1 and 2, performed were a film thickness test per film formation time and a test for determination of step coverage.

First, silicon substrates having $SiO_2$ film with thickness 5000 Å over surface thereof were prepared five by five and mounted in the film formation chamber of the MOCVD apparatus as shown in FIG. 5. Next, temperature of the substrate was set to be 200° C. while vaporization temperature to be 140° C., and pressure to be about 266 Pa (2 Torr). $O_2$ gas was used as the reaction gas with 100 ccm of partial pressure. Subsequently, Ar gas was used as the carrier gas and the solution material was supplied in a flow rate of 0.05 cc/min. When the film formation time reached 1, 5, 10, 20 and 30 minutes, the sheets were taken out one by one from the film formation chamber.

(1) Film Thickness Test Per Film Formation Time

The hafnium oxide thin film over the substrate after completion of the film formation was determined for film thickness from SEM (Scanning Electron Microscope) image.

(2) Test for Step Coverage

Figure 6:
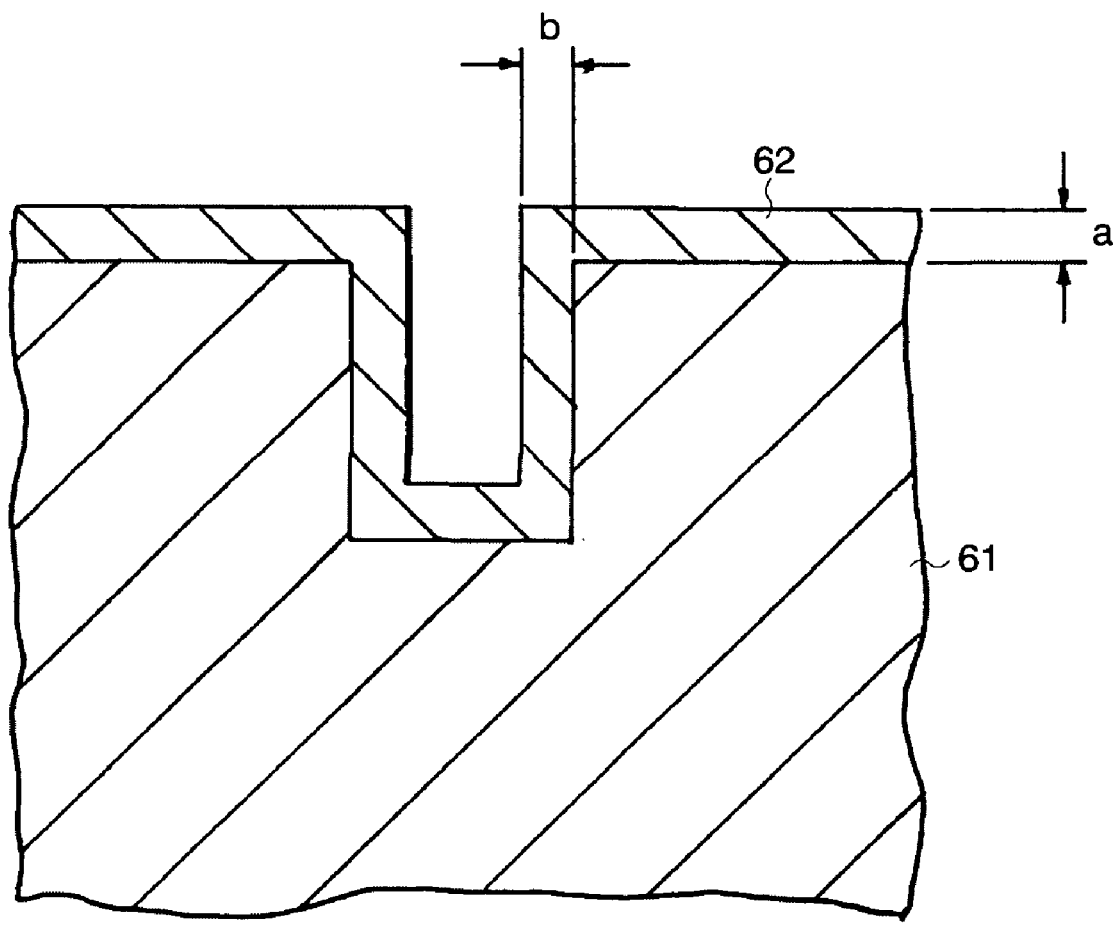
FIG. 6 is a sectional view of a substrate illustrating a calculation procedure to determine step coverage rate of film obtained by MOCVD process.

The hafnium oxide thin film over the substrate after completion of the film formation was determined for step coverage from SEM (Scanning Electron Microscope) image. The step coverage is represented by a/b value when the substrate 61 having level difference such as grooves shown in FIG. 6 is coated with a thin film 62. If the a/b value is 1.0, it is considered that the step coverage is good because inner portions of grooves in the substrate as well as flat portion thereof were evenly coated with the thin film. If the a/b is less than 1.0, the inner portions of the grooves has a film formation level greater than that of the flat portion of the substrate. Whereas the a/b is more than 1.0, it is difficult to accomplish the film formation even for the inner portions of the substrate, thereby resulting in poor step coverage.

Evaluation

The results of tests for the hafnium-containing materials for film formation obtained in Examples 1 to 7 and Comparative Examples 1 and 2 such as contents of respective impurities, film thickness per film formation time and step coverage are shown in Tables 1 and 2.

TABLE 1

| | Organohafnium compound | Zr content (ppm) | Alkali metal content (ppm) | Alkaline-earth metal content (ppm) | Content of each of metal elements (ppm) | | | | | | Total content |
|---|---|---|---|---|---|---|---|---|---|---|---|
| | | | | | Fe | Zn | Ti | Al | Cr | Ni | |
| Ex. 1 | Hf(Et$_2$N)$_4$ | 500 | 0.5 | 0.8 | 0.1 | 0.2 | 0.1 | 0.1 | 0.1 | 0.1 | 0.7 |
| Ex. 2 | Hf(Et$_2$N)$_4$ | 100 | 0.1 | 0.5 | 0.1 | 0.1 | 0.1 | 0.1 | 0.1 | 0.2 | 0.7 |
| Ex. 3 | Hf(Et$_2$N)$_4$ | 50 | 0.2 | 0.5 | 0.1 | 0.2 | 0.2 | 0.1 | 0.1 | 0.1 | 0.8 |
| Ex. 4 | Hf(Et$_2$N)$_4$ | 10 | 0.3 | 0.2 | 0.1 | 0.1 | 0.1 | 0.1 | 0.1 | 0.1 | 0.6 |
| Ex. 5 | Hf(Et$_2$N)$_4$ | 5 | 0.5 | 0.1 | 0.1 | 0.1 | 0.2 | 0.2 | 0.1 | 0.1 | 0.8 |
| Ex. 6 | Hf(Et$_2$N)$_4$ | <5 | 0.1 | 0.3 | 0.01 | 0.01 | 0.1 | 0.02 | 0.01 | 0.01 | 0.16 |
| Ex. 7 | Hf(Et$_2$N)$_4$ | 650 | 0.1 | 0.7 | 0.01 | 0.01 | 0.1 | 0.02 | 0.01 | 0.01 | 0.16 |
| Comp. Ex. 1 | Hf(Et$_2$N)$_4$ | >1000 | 8 | 10 | 3 | 1 | 5 | 2 | 0.1 | 2 | 13.1 |
| Comp. Ex. 2 | Hf(Et$_2$N)$_4$ | 700 | 5 | 2 | 8 | 5 | 10 | 1 | 2 | 1 | 27 |

TABLE 2

| | Organohafnium compound | Film thickness per film formation time (nm) | | | | | Step coverage (—) | | | | |
|---|---|---|---|---|---|---|---|---|---|---|---|
| | | 1 min | 5 min | 10 min | 20 min | 30 min | 1 min | 5 min | 10 min | 20 min | 30 min |
| Ex. 1 | Hf(Et$_2$N)$_4$ | 0.02 | 0.1 | 0.18 | 0.38 | 0.57 | 0.7 | 0.8 | 0.8 | 0.9 | 1 |
| Ex. 2 | Hf(Et$_2$N)$_4$ | 0.1 | 0.5 | 0.9 | 1.8 | 2.8 | 0.9 | 1 | 1.1 | 0.9 | 1 |
| Ex. 3 | Hf(Et$_2$N)$_4$ | 0.18 | 0.8 | 2 | 3.5 | 5.5 | 0.9 | 0.9 | 1 | 1.1 | 1 |
| Ex. 4 | Hf(Et$_2$N)$_4$ | 0.5 | 2.5 | 4.8 | 10.1 | 14.8 | 0.8 | 0.8 | 0.9 | 1 | 0.9 |
| Ex. 5 | Hf(Et$_2$N)$_4$ | 0.8 | 3.8 | 7.8 | 15.8 | 25 | 0.9 | 0.9 | 0.8 | 1 | 0.9 |
| Ex. 6 | Hf(Et$_2$N)$_4$ | 1.2 | 5.9 | 13 | 24 | 35 | 1.1 | 1 | 0.9 | 1 | 0.9 |
| Ex. 7 | Hf(Et$_2$N)$_4$ | 0.02 | 0.08 | 0.18 | 0.40 | 0.50 | 0.8 | 0.8 | 0.7 | 0.9 | 1.0 |
| Comp. Ex. 1 | Hf(Et$_2$N)$_4$ | 0.01 | 0.015 | 0.013 | 0.02 | 0.024 | 0.1 | 0.01 | 0.011 | 0.009 | 0.0007 |
| Comp. Ex. 2 | Hf(Et$_2$N)$_4$ | 0.02 | 0.012 | 0.013 | 0.011 | 0.034 | 0.1 | 0.05 | 0.02 | 0.02 | 0.02 |

As clearly shown from the above Tables 1 and 2, it was found that the thin film obtained by using the hafnium-containing materials for film formation in Comparative Examples 1 and 2 did not exhibit increase of thickness of the film even when time passed, and thus, it had poor stability in film formation. Also, it showed the result that the step coverage is extremely poor. Therefore, it is apprehended that if a gate oxide film is formed over the substrate having grooves by using the hafnium-containing materials for the film formation obtained in Comparative Examples 1 and 2, it causes generation of voids. While, the thin film which was formed using the hafnium-containing materials for film formation obtained in Examples 1 to 7 had extremely higher film formation rate and uniform thickness per film formation time, compared to the materials according to Comparative Examples 1 and 2. As a result, the thin film showed the improved film formation stability. Furthermore, it was found that the thin film was uniformly coated in even inner portion of the grooves as well as the flat portions of the substrate since the value of the step coverage was close to 1.0.

Example 8

First, diethylaminolithium was synthesized from n-butyl-lithium and diethylamine. Next, a crude product of $Hf(Et_2N)_4$ was obtained by preparing hafnium tetrachloride which is commercially available and contains 1000 ppm or more of Zr element, adding to the above hafnium tetrachloride the obtained diethylaminolithium in an amount of 4 times moles to form a solution and reacting the solution for 30 minutes under ice-cooling. Then, after returning the crude product to room temperature, a purified product of $Hf(Et_2N)_4$ was obtained by carrying out distillation and purification of the crude product under reduced pressure and at about 100° C. and about 3.99 kPa (30 Torr).

Subsequently, inside a pressure-resistant column 21 of a flash chromatography apparatus 20 as shown in FIG. 3, a filler layer 22 was formed by charging 800 g of a filler carrying a chelating agent. As the chelating agent, acetylacetone was used. The filler was alumina particles having a mean particle diameter of 0.5 μm and a particle size distribution $d_{90}/d_{10}$ of 0.8. An Erlenmeyer flask 23 was kept under an inert gas atmosphere by introducing Ar gas through one side 23b of an opening part into the flask and exhausting it out of the other side 23c thereof. A top cover 21b of the column 21 was opened, followed by introducing a purified product of $Hf(Et_2N)_4$ through upper portion of the filler layer 22. Next, by closing the cover 21b of the column 21, and then supplying the Ar gas with a column flow rate ranging from 2 to 4 cm/min in terms of space velocity (SV value) out of a gas inlet 21c inside the column, passed was the purified product through the filler layer 22. After passing through the filler layer 22, the purified product was collected in the Erlenmeyer flask 23 through an outlet 21a which is formed at a lower part of the column 21.

Then, prepared was $(Me_2N)_4Si$ as an organosilicon compound. The $Hf(Et_2N)_4$ and $(Me_2N)_4Si$ were collected in the Erlenmeyer flask 23 and blended in a weight ratio of 5:1 of the organosilicon compound: the organohafnium compound to form a mixture. As a result of determination of the Zr content in the obtained mixture by means of UV-VIS absorption spectrum analysis, the Zr content was 500 ppm. The resultant mixture comprising $Hf(Et_2N)_4$ and $(Me_2N)_4Si$ with 500 ppm of Zr content was used as the hafnium-containing material for film formation.

Example 9

$Hf(Et_2N)_4$ was prepared in the same manner as in Example 8, except that dipivaloyl methane was used as the chelating agent. $(Me_2N)_4Si$ was prepared as an organosilicon compound, and $Hf(Et_2N)_4$ and $(Me_2N)_4Si$ were blended in a weight ratio of 3:1 of the organosilicon compound: the organohafnium compound to form a mixture. As a result of determination of the Zr content in the obtained mixture by means of UV-VIS absorption spectrum analysis, the Zr content was 100 ppm. The resultant mixture comprising $Hf(Et_2N)_4$ and $(Me_2N)_4Si$ with 100 ppm of Zr content was used as the hafnium-containing material for film formation.

Example 10

$Hf(Et_2N)_4$ was prepared in the same manner as in Example 8, except that EDTA was used as the chelating agent. $(Me_2N)_4Si$ was prepared as an organosilicon compound, and $Hf(Et_2N)_4$ and $(Me_2N)_4Si$ were blended in a weight ratio of 2:1 of the organosilicon compound: the organohafnium compound to form a mixture. As a result of determination of the Zr content in the obtained mixture by means of UV-VIS absorption spectrum analysis, the Zr content was 50 ppm. The resultant mixture comprising $Hf(Et_2N)_4$ and $(Me_2N)_4Si$ with 50 ppm of Zr content was used as the hafnium-containing material for film formation.

Example 11

$Hf(Et_2N)_4$ was prepared in the same manner as in Example 8, except that hexafluoroacetylacetone was used as the chelating agent. $(Me_2N)_4Si$ was prepared as an organosilicon compound, and $Hf(Et_2N)_4$ and $(Me_2N)_4Si$ were blended in a weight ratio of 1:1 of the organosilicon compound: the organohafnium compound to form a mixture. As a result of determination of the obtained mixture for Zr content by means of UV-VIS absorption spectrum analysis, the Zr content was 10 ppm. The resultant mixture comprising $Hf(Et_2N)_4$ and $(Me_2N)_4Si$ with 10 ppm of Zr content was used as the hafnium-containing material for film formation.

Example 12

$Hf(Et_2N)_4$ was prepared in the same manner as in Example 8, except that TOPO was used as the chelating agent. $(Me_2N)_4Si$ was prepared as an organosilicon compound, and $Hf(Et_2N)_4$ and $(Me_2N)_4Si$ were blended in a weight ratio of 4:1 of the organosilicon compound: the organohafnium compound to form a mixture. As a result of determination of the Zr content in the obtained mixture by means of UV-VIS absorption spectrum analysis, the Zr content was 5 ppm. The resultant mixture comprising $Hf(Et_2N)_4$ and $(Me_2N)_4Si$ with 5 ppm of Zr content was used as the hafnium-containing material for film formation.

Example 13

$Hf(Et_2N)_4$ was prepared in the same manner as in Example 8, except that DTPA was used as the chelating agent. $(Me_2N)_4Si$ was prepared as an organosilicon compound, and $Hf(Et_2N)_4$ and $(Me_2N)_4Si$ were blended in a weight ratio of 1:3 of the organosilicon compound: the organohafnium compound to form a mixture. As a result of determination of the obtained mixture for Zr content by means of UV-VIS absorption spectrum analysis, the Zr content was less than 5 ppm. The resultant mixture comprising $Hf(Et_2N)_4$ and $(Me_2N)_4Si$ with less than 5 ppm of Zr content was used as the hafnium-containing material for film formation.

Example 14

$Hf(Et_2N)_4$ was prepared in the same manner as in Example 8, except that IDA was used as the chelating agent. $(Me_2N)_4Si$ was prepared as an organosilicon compound, and $Hf(Et_2N)_4$ and $(Me_2N)_4Si$ were blended in a weight ratio of 1:5 of the organosilicon compound: the organohafnium compound to form a mixture. As a result of determination of the Zr content in the obtained mixture by means of UV-VIS absorption spectrum analysis, the Zr content was 650 ppm. The resultant mixture comprising $Hf(Et_2N)_4$ and $(Me_2N)_4Si$ with 650 ppm of Zr content was used as the hafnium-containing material for film formation.

Comparative Example 3

$Hf(Et_2N)_4$ was prepared in the same manner as in Comparative Example 1. $(Me_2N)_4Si$ was prepared as an organosilicon compound, and $Hf(Et_2N)_4$ and $(Me_2N)_4Si$ were blended in a weight ratio of 2:1 of the organosilicon compound: the organohafnium compound to form a mixture. As a result of determination of the obtained mixture for Zr content by means of UV-VIS absorption spectrum analysis, the Zr content exceeded 1000 ppm. The resultant mixture comprising $Hf(Et_2N)_4$ and $(Me_2N)_4Si$ with more than 1000 ppm of Zr content was used as the hafnium-containing material for film formation.

Comparative Example 4

$Hf(Et_2N)_4$ was prepared in the same manner as in Example 1, except that the ligroin extraction was 5 times repeated. Next, $(Me_2N)_4Si$ was prepared as an organosilicon compound, and $Hf(Et_2N)_4$ and $(Me_2N)_4Si$ were blended in a weight ratio of 3:1 of the organosilicon compound: the organohafnium compound to form a mixture. As a result of determination of the Zr content in the obtained mixture by means of UV-VIS absorption spectrum analysis, the Zr content was 700 ppm. The resultant mixture comprising $Hf(Et_2N)_4$ and $(Me_2N)_4Si$ with 700 ppm of Zr content was used as the hafnium-containing material for film formation.

Comparative Evaluation 3

By using each of the hafnium-containing materials obtained in Examples 8 to 14 and Comparative Examples 3 and 4, performed were a film thickness test per film formation time and a for determination of step coverage.

First, silicon substrates having $SiO_2$ film with thickness 5000 Å over surface thereof were prepared five by five and mounted in the film formation chamber of the MOCVD apparatus as shown in FIG. 5. Next, temperature of the substrate was set to be 200° C. while vaporization temperature to be 140° C., and pressure to be about 266 Pa (2 Torr). $O_2$ gas was used as the reaction gas with 100 ccm of partial pressure. Subsequently, Ar gas was used as the carrier gas and the solution material was supplied in a flow rate of 0.05 cc/min. When the film formation time reached to 1, 5, 10, 20 and 30 minutes, the sheets were taken out one by one from the film formation chamber.

(1) Film Thickness Test Per Film Formation Time

The Si—O—Hf thin film over the substrate after completion of the film formation was determined for film thickness from SEM (Scanning Electron Microscope) image.

(2) Test for Step Coverage

The Si—O—Hf thin film over the substrate after completion of the film formation was determined for step coverage from SEM (Scanning Electron Microscope) image.

Evaluation

The results of tests for the hafnium-containing materials for film formation obtained in Examples 8 to 14 and Comparative Examples 3 and 4 such as contents of respective impurities, film thickness per film formation time and step coverage are shown in Tables 3 and 4.

TABLE 3

| | Organohafnium compound | Organic Si compound | Compounding ratio (wt. ratio) | Zr content (ppm) | Content of each of metal elements (ppm) | | | | | | Total content |
|---|---|---|---|---|---|---|---|---|---|---|---|
| | | | | | Fe | Zn | Ti | Al | Cr | Ni | |
| Ex. 8 | $Hf(Et_2N)_4$ | $(Me_2N)_4Si$ | 5:1 | 500 | 0.1 | 0.1 | 0.05 | 0.1 | 0.1 | 0.05 | 0.5 |
| Ex. 9 | | | 3:1 | 100 | 0.2 | 0.1 | 0.1 | 0.1 | 0.1 | 0.05 | 0.65 |
| Ex. 10 | | | 2:1 | 50 | 0.1 | 0.1 | 0.1 | 0.1 | 0.1 | 0.1 | 0.6 |
| Ex. 11 | | | 1:1 | 10 | 0.1 | 0.2 | 0.05 | 0.05 | 0.05 | 0.05 | 0.5 |
| Ex. 12 | | | 4:1 | 5 | 0.1 | 0.1 | 0.1 | 0.1 | 0.1 | 0.1 | 0.6 |
| Ex. 13 | | | 1:3 | <5 | 0.1 | 0.2 | 0.01 | 0.05 | 0.1 | 0.1 | 0.56 |
| Ex. 14 | | | 1:5 | 650 | 0.1 | 0.1 | 0.1 | 0.1 | 0.1 | 0.1 | 0.6 |
| Comp. Ex. 3 | $Hf(Et_2N)_4$ | $(Me_2N)_4Si$ | 2:1 | >1000 | 2 | 5 | 3 | 1 | 2 | 1 | 14 |
| Comp. Ex. 4 | | | 3:1 | 700 | 3 | 2 | 1 | 5 | 2 | 1 | 14 |

TABLE 4

| | Alkali metal content (ppm) | Alkaline-earth metal content (ppm) | Film thickness per film formation time (nm) | | | | | Step coverage (–) | | | | |
|---|---|---|---|---|---|---|---|---|---|---|---|---|
| | | | 1 min | 5 min | 10 min | 20 min | 30 min | 1 min | 5 min | 10 min | 20 min | 30 min |
| Ex. 8 | 0.3 | 0.1 | 0.1 | 0.5 | 1.0 | 1.8 | 2.9 | 0.8 | 0.9 | 0.9 | 1.0 | 1.0 |
| Ex. 9 | 0.1 | 0.3 | 0.1 | 0.5 | 1.0 | 2.0 | 3.0 | 0.8 | 0.9 | 1.0 | 0.9 | 1.0 |
| Ex. 10 | 0.2 | 0.3 | 0.2 | 0.9 | 2.0 | 4.0 | 5.9 | 0.9 | 1.0 | 1.0 | 0.8 | 1.0 |
| Ex. 11 | 0.2 | 0.4 | 0.8 | 3.9 | 7.8 | 15.9 | 23.8 | 0.9 | 1.0 | 0.8 | 0.9 | 0.8 |
| Ex. 12 | 0.1 | 0.7 | 0.5 | 2.5 | 4.9 | 10 | 15.0 | 0.8 | 1.0 | 1.0 | 0.9 | 1.0 |
| Ex. 13 | 0.1 | 0.5 | 1.0 | 4.8 | 9 | 19 | 28 | 0.9 | 1.0 | 1.0 | 0.9 | 1.0 |
| Ex. 14 | 0.4 | 0.8 | 0.01 | 0.05 | 0.12 | 0.2 | 0.3 | 1.0 | 0.9 | 0.9 | 0.8 | 1.0 |
| Comp. Ex. 3 | 8 | 10 | 0.001 | 0.001 | 0.004 | 0.002 | 0.001 | 0.1 | 0.01 | 0.011 | 0.001 | 0.0005 |
| Comp. Ex. 4 | 5 | 2 | 0.002 | 0.003 | 0.004 | 0.003 | 0.001 | 0.1 | 0.01 | 0.01 | 0.01 | 0.009 |

As clearly shown in the above Tables 3 and 4, it was found that the thin film obtained by using the hafnium-containing materials in Comparative Examples 3 and 4 did not exhibit increase of thickness of the film even when time passed, and thus, it had poor stability in film formation. Also, it showed the result that the step coverage is extremely poor. Therefore, it is apprehended that if a gate oxide film is formed over the substrate having grooves by using the hafnium-containing materials for the film formation obtained in Comparative Examples 3 and 4, it causes generation of voids. While, the thin film which was formed using the hafnium-containing materials for film formation obtained in Examples 8 to 14 had extremely higher film formation rate and uniform thickness distribution per film formation time, compared to the materials according to Comparative Examples 3 and 4. As a result, the thin film showed the improved film formation stability. Furthermore, it was found that the thin film was uniformly coated in even inner portion of the grooves as well as the flat portions of the substrate since the value of the step coverage was close to 1.0.

Example 15

Aminolithium was prepared by reaction of n-butyllithium and dimethylamine. Next, prepared was hafnium tetrachloride which is commercially available and contains 1000 ppm or more of the Zr element. For the hafnium tetrachloride, an impurity removal process was conducted. First, inside a pressure-resistant column 21 of a flash chromatography apparatus 20 as shown in FIG. 3, a filler layer 22 was formed by charging 500 g of hafnium tretrachloride. As the chelating agent, acetylacetone was used. After introducing the chelating agent into the column 21, the chelating agent naturally flowed down and passed through the filler layer 22. After passing the chelating agent through the filler layer 22, closed was the outlet 21a at lower portion of the column 21 and the hafnium tetrachloride was taken out of the column 21 by means of vacuum treatment, etc. The obtained hafnium tetrachloride was washed with hexane. Thereafter, impurities in the hafnium tetrachloride were removed.

Next, to the purified hafnium tetrachloride after removal of the impurities was added the aminolithium in a molar amount of times of a valence followed by keeping the solution for 30 minutes under ice-cooling to accelerate the reaction to obtain a crude product of $Hf(Me_2N)_4$. Then, after returning the crude product to room temperature, a purified product of Hf $(Me_2N)_4$ was obtained by carrying out distillation and purification of the crude product under reduced pressure and at about 100° C. and about 3.99 kPa (30 Torr). Then, prepared was $[(Me_2N)_2MeSi—]_2$ as an organosilicon compound. $Hf(Me_2N)_4$ and $[(Me_2N)_2MeSi—]_2$ were blended in a weight ratio of 1:3 of the organosilicon compound: the organohafnium compound to form a mixture. As a result of determination of the Zr content in the obtained mixture by means of UV-VIS absorption spectrum analysis, the Zr content was 500 ppm. The resultant mixture comprising $Hf(Me_2N)_4$ and $[(Me_2N)_2MeSi—]_2$ with 500 ppm of Zr content was used as the hafnium-containing material for film formation.

Example 16

$Hf(Me_2N)_4$ was prepared in the same manner as in Example 15, except that dipivaloyl methane was used as the chelating agent. $[(Me_2N)_2MeSi—]_2$ was prepared as an organosilicon compound, and $Hf(Me_2N)_4$ and $[(Me_2N)_2MeSi—]_2$ were blended in a weight ratio of 3:1 of the organosilicon compound: the organohafnium compound to form a mixture. As a result of determination of the obtained mixture for Zr content by means of UV-VIS absorption spectrum analysis, it was evident that the Zr content was 100 ppm. The resultant mixture comprising $Hf(Me_2N)_4$ and $[(Me_2N)_2MeSi—]_2$ with 100 ppm of Zr content was used as the hafnium-containing material for film formation.

Example 17

Hf $(Me_2N)_4$ was prepared in the same manner as in Example 15, except that EDTA was used as the chelating agent. $[(Me_2N)_2MeSi—]_2$ was prepared as an organosilicon compound, and $Hf(Me_2N)_4$ and $[(Me_2N)_2MeSi—]_2$ were blended in a weight ratio of 2:1 of the organosilicon compound: the organohafnium compound to form a mixture. As a result of determination of the obtained mixture for Zr content by means of UV-VIS absorption spectrum analysis, the Zr content was 50 ppm. The resultant mixture comprising Hf(Me$_2$N)$_4$ and [(Me$_2$N)$_2$MeSi—]$_2$ with 50 ppm of Zr content was used as the hafnium-containing material for film formation.

Example 18

Hf(Me$_2$N)$_4$ was prepared in the same manner as in Example 15, except that hexafluoroacetylacetone was used as the chelating agent. [(Me$_2$N)$_2$MeSi—]$_2$ was prepared as an organosilicon compound, and Hf(Me$_2$N)$_4$ and [(Me$_2$N)$_2$MeSi—]$_2$ were blended in a weight ratio of 1:1 of the organosilicon compound: the organohafnium compound to form a mixture. As a result of determination of the obtained mixture for Zr content by means of UV-VIS absorption spectrum analysis, it was evident that the Zr content was 10 ppm. The resultant mixture comprising Hf(Me$_2$N)$_4$ and [(Me$_2$N)$_2$MeSi—]$_2$ with 10 ppm of Zr content was used as the hafnium-containing material for film formation.

Example 19

Hf(Me$_2$N)$_4$ was prepared in the same manner as in Example 15, except that TOPO was used as the chelating agent. [(Me$_2$N)$_2$MeSi—]$_2$ was prepared as an organosilicon compound, and Hf(Me$_2$N)$_4$ and [(Me$_2$N)$_2$MeSi—]$_2$ were blended in a weight ratio of 4:1 of the organosilicon compound: the organohafnium compound to form a mixture. As a result of determination of the obtained mixture for Zr content by means of UV-VIS absorption spectrum analysis, the Zr content was 5 ppm. The resultant mixture comprising Hf(Me$_2$N)$_4$ and [(Me$_2$N)$_2$MeSi—]$_2$ with 5 ppm of Zr content was used as the hafnium-containing material for film formation.

Example 20

Hf(Me$_2$N)$_4$ was prepared in the same manner as in Example 15, except that DTPA was used as the chelating agent. [(Me$_2$N)$_2$MeSi—]$_2$ was prepared as an organosilicon compound, and Hf(Me$_2$N)$_4$ and [(Me$_2$N)$_2$MeSi—]$_2$ were blended in a weight ratio of 1:3 of the organosilicon compound: the organohafnium compound to form a mixture. As a result of determination of the obtained mixture for Zr content by means of UV-VIS absorption spectrum analysis, the Zr content was less than 5 ppm. The resultant mixture comprising Hf(Me$_2$N)$_4$ and [(Me$_2$N)$_2$MeSi—]$_2$ with less than 5 ppm of Zr content was used as the hafnium-containing material for film formation.

Example 21

Hf(Me$_2$N)$_4$ was prepared in the same manner as in Example 15, except that IDA was used as the chelating agent. [(Me$_2$N)$_2$MeSi—]$_2$ was prepared as an organosilicon compound, and Hf(Me$_2$N)$_4$ and [(Me$_2$N)$_2$MeSi—]$_2$ were blended in a weight ratio of 1:5 of the organosilicon compound: the organohafnium compound to form a mixture. As a result of determination of the obtained mixture for Zr content by means of UV-VIS absorption spectrum analysis, the Zr content was 650 ppm. The resultant mixture comprising Hf(Me$_2$N)$_4$ and [(Me$_2$N)$_2$MeSi—]$_2$ with 650 ppm of Zr content was used as the hafnium-containing material for film formation.

Comparative Example 5

First, dimethylaminolithium was synthesized from n-butyllithium and dimethylamine. Next, prepared was hafnium tetrachloride which is commercially available and contains 1000 ppm or more of the Zr element. To this hafnium tetrachloride was added dimethylaminolithium in an amount of 4 times moles followed by keeping the solution for about 30 minutes under ice-cooling to accelerate the reaction to obtain a crude product of Hf(Me$_2$N)$_4$. Then, after returning the crude product to room temperature, a purified product of Hf(Me$_2$N)$_4$ was obtained by carrying out distillation and purification of the crude product under reduced pressure at 100° C. and 3.99 kPa (30 Torr).

Then, prepared was [(Me$_2$N)$_2$MeSi—]$_2$ as an organosilicon compound, and Hf(Me$_2$N)$_4$ and [(Me$_2$N)$_2$MeSi—]$_2$ were blended in a weight ratio of 3:1 of the organosilicon compound: the organohafnium compound to form a mixture. As a result of determination of the obtained mixture for Zr content by means of UV-VIS absorption spectrum analysis, the Zr content exceeded 1000 ppm. The resultant mixture comprising Hf(Me$_2$N)$_4$ and [(Me$_2$N)$_2$MeSi—]$_2$ with more than 1000 ppm of Zr content was used as the hafnium-containing material for film formation.

Comparative Example 6

Hf (Me$_2$N)$_4$ was prepared in the same manner as in Example 1, except that diethylamine was replaced by dimethylamine and the ligroin extraction was 5 times repeated. Next, [(Me$_2$N)$_2$MeSi—]$_2$ was prepared as an organosilicon compound, and Hf(Me$_2$N)$_4$ and [(Me$_2$N)$_2$MeSi—]$_2$ were blended in a weight ratio of 3:1 of the organosilicon compound: the organohafnium compound to form a mixture. As a result of determination of the obtained mixture for Zr content by means of UV-VIS absorption spectrum analysis, the Zr content was 700 ppm. The resultant mixture comprising Hf(Me$_2$N)$_4$ and [(Me$_2$N)$_2$MeSi—]$_2$ with 700 ppm of Zr content was used as the hafnium-containing material for film formation.

Comparative Evaluation 4

By using each of the hafnium-containing materials for film formation obtained in Examples 15 to 21 and Comparative Examples 5 and 6, performed were a film thickness test per film formation time and a test for determination of step coverage.

First, silicon substrates having SiO$_2$ film with thickness 5000 Å over surface thereof were prepared five by five and mounted in the film formation chamber of the MOCVD apparatus as shown in FIG. 5. Next, temperature of the substrate was set to be 200° C. while vaporization temperature to be 140° C., and pressure to be about 266 Pa (2 Torr). O$_2$ gas was used as the reaction gas with 100 ccm of partial pressure. Subsequently, Ar gas was used as the carrier gas and the solution material was supplied in a flow rate of 0.05 cc/min. When the film formation time reached to 1, 5, 10, 20 and 30 minutes, the sheets were taken out one by one from the film formation chamber.

(1) Film Thickness Test Per Film Formation Time

The Si—O—Hf thin film over the substrate after completion of the film formation was determined for film thickness from SEM (Scanning Electron Microscope) image.

(2) Test for Step Coverage

The Si—O—Hf thin film over the substrate after completion of the film formation was determined for step coverage from SEM (Scanning Electron Microscope) image.

Evaluation

The results of tests for the hafnium-containing materials for film formation obtained in Examples 15 to 21 and Comparative Examples 5 and 6 such as contents of respective impurities, film thickness per film formation time and step coverage are shown in Tables 5 and 6.

surface. While, the thin film which was formed using the hafnium-containing materials for film formation obtained in Examples 15 to 21 had extremely higher film formation rate and uniform thickness per film formation time, compared to the materials according to Comparative Examples 5 and 6. As a result, the thin film showed the improved film formation stability. Furthermore, it was found that the thin film

TABLE 5

| | Organohafnium compound | Organic Si compound | Compounding ratio (wt. ratio) | Zr content (ppm) | Content of each of metal elements (ppm) | | | | | | |
|---|---|---|---|---|---|---|---|---|---|---|---|
| | | | | | Fe | Zn | Ti | Al | Cr | Ni | Total content |
| Ex. 15 | Hf(Me$_2$N)$_4$ | [(Me$_2$N)$_2$MeSi—]$_2$ | 1:3 | 500 | 0.1 | 0.2 | 0.05 | 0.05 | 0.05 | 0.05 | 0.5 |
| Ex. 16 | | | 3:1 | 100 | 0.2 | 0.1 | 0.1 | 0.1 | 0.1 | 0.1 | 0.7 |
| Ex. 17 | | | 2:1 | 50 | 0.1 | 0.1 | 0.1 | 0.01 | 0.01 | 0.1 | 0.42 |
| Ex. 18 | | | 1:1 | 10 | 0.1 | 0.1 | 0.1 | 0.1 | 0.1 | 0.1 | 0.6 |
| Ex. 19 | | | 4:1 | 5 | 0.01 | 0.01 | 0.1 | 0.1 | 0.1 | 0.1 | 0.42 |
| Ex. 20 | | | 1:3 | <5 | 0.1 | 0.1 | 0.1 | 0.1 | 0.1 | 0.1 | 0.6 |
| Ex. 21 | | | 1:5 | 650 | 0.1 | 0.1 | 0.05 | 0.05 | 0.05 | 0.05 | 0.4 |
| Comp. Ex. 5 | Hf(Me$_2$N)$_4$ | [(Me$_2$N)$_2$MeSi—]$_2$ | 3:1 | >1000 | 1 | 1 | 1 | 0.1 | 3 | 5 | 11.1 |
| Comp. Ex. 6 | | | 3:1 | 700 | 3 | 2 | 1 | 0.9 | 1 | 2 | 9.9 |

TABLE 6

| | Alkali metal content (ppm) | Alkaline-earth metal content (ppm) | Film thickness per film formation time (nm) | | | | | Step coverage (−) | | | | |
|---|---|---|---|---|---|---|---|---|---|---|---|---|
| | | | 1 min | 5 min | 10 min | 20 min | 30 min | 1 min | 5 min | 10 min | 20 min | 30 min |
| Ex. 15 | 0.1 | 0.1 | 0.2 | 1.0 | 2.0 | 4.0 | 6.0 | 0.9 | 0.8 | 1.0 | 0.8 | 0.9 |
| Ex. 16 | 0.1 | 0.1 | 0.2 | 0.9 | 2.0 | 3.8 | 5.8 | 1.0 | 0.9 | 0.9 | 0.9 | 1.0 |
| Ex. 17 | 0.3 | 0.1 | 0.1 | 0.5 | 1.1 | 2.1 | 3.3 | 1.0 | 0.9 | 0.8 | 1.0 | 1.0 |
| Ex. 18 | 0.2 | 0.1 | 0.3 | 1.5 | 3.0 | 5.8 | 9.0 | 1.0 | 0.9 | 1.0 | 1.0 | 0.9 |
| Ex. 19 | 0.3 | 0.2 | 0.1 | 0.5 | 1.0 | 2.0 | 3.0 | 0.8 | 0.9 | 1.0 | 1.0 | 0.9 |
| Ex. 20 | 0.3 | 0.1 | 0.3 | 1.4 | 2.8 | 5.8 | 8.5 | 0.9 | 1.0 | 0.9 | 0.9 | 0.9 |
| Ex. 21 | 0.1 | 0.4 | 0.5 | 2.4 | 4.9 | 10.0 | 15.0 | 0.9 | 1.0 | 0.9 | 1.0 | 1.0 |
| Comp. Ex. 5 | 5.6 | 10.5 | 0.001 | 0.001 | 0.0009 | 0.001 | 0.0006 | 0.1 | 0.1 | 0.3 | 0.1 | 0.001 |
| Comp. Ex. 6 | 9.8 | 3 | 0.001 | 0.001 | 0.0008 | 0.002 | 0.001 | 0.2 | 0.1 | 0.2 | 0.01 | 0.002 |

As clearly shown from the above Tables 5 and 6, it was clearly found that the thin film obtained by using the hafnium-containing materials for film formation in Comparative Examples 5 and 6 did not exhibit increase of thickness of the film even when time passed, and thus, it had poor stability in film formation. Also, it showed the result that the step coverage is extremely poor. Therefore, it is apprehended that if a gate oxide film is formed over the substrate having grooves by using the hafnium-containing materials for the film formation obtained in Comparative Examples 5 and 6, it causes generation of voids on the was uniformly coated in even inner portion of the grooves as well as the flat portions of the substrate since the value of the step coverage was close to 1.0.

Examples 22 to 26

First, hafnium tetrachloride which is commercially available and contains 1000 ppm or more of Zr element and absolute ether were prepared. A suspension was prepared by suspending the above hafnium tetrachloride in absolute ether. Also, prepared were spherical sintered activated carbon with a particle size of 1 mmφ and zirconium pieces were subjected to electrolytic polishing and back-side treatment with hydrogen peroxide, respectively. Thereafter, the sintered activated carbon was added to the above suspension, followed by stirring the resultant product at room temperature for 24 hours. Next, the above zirconium pieces obtained were put into the suspension containing the sintered activated carbon. Then, the suspension was subjected to light irradiation using UV light having wavelength of about 264 nm for about 5 minutes to generate photoreaction. After the light irradiation, the a sintered activated carbon and the zirconium pieces were separated by filtration from the suspension then the residual suspension was concentrated to remove the ether component. In addition, by means of microfiltration using porous filter having 0.2 µm pore size, obtained was a purified product of hafnium tetrachloride. Further, the purified hafnium tetrachloride product, n-butyllithium and n-butanol were reacted in a stoichiometric ratio in tetrahydrofuran to obtain $Hf(OnBu)_4$. Also, by varying UV light irradiation times to 30 minutes, 2 hours, 3 hours and 4 hours, $Hf(OnBu)_4$ products were prepared, respectively. As a result of determination of the Zr content in the obtained $Hf(OnBu)_4$ by means of UV-VIS absorption spectrum analysis, the Zr contents were 650 ppm, 200 ppm, 100 ppm, 50 ppm and 20 ppm, respectively. These $Hf(OnBu)_4$ products were used as the hafnium-containing materials for film formation.

Comparative Examples 7 to 11

Each $Hf(OnBu)_4$ was prepared in the same manner as in Example 22, except that UV light irradiation time was varied to 1 minutes, 40 seconds, 30 seconds, 20 seconds and 10 seconds. As a result of determination of the Zr content in the obtained $Hf(OnBu)_4$ by means of UV-VIS absorption spectrum analysis, the Zr contents were 700 ppm, 1000 ppm, 1500 ppm, 2000 ppm and more than 2000 ppm, respectively. The $Hf(OnBu)_4$ products were used as the hafnium-containing materials for film formation.

Examples 27 to 31

Each $Hf(OnPr)_4$ was prepared in the same manner as in Examples 22 to 26, except that n-butyllithium was replaced by n-propyl lithium. As a result of determination the Zr content in the obtained $Hf(OnPr)_4$ by means of UV-VIS absorption spectrum analysis, the Zr contents were 650 ppm, 200 ppm, 100 ppm, 50 ppm and 20 ppm, respectively. These $Hf(OnPr)_4$ were used as the hafnium-containing materials for film formation.

Comparative Examples 12 to 16

Each $Hf(OnPr)_4$ was prepared in the same manner as in Example 27, except that UV light irradiation time was varied to 1 minutes, 40 seconds, 30 seconds, 20 seconds and 10 seconds. As a result of determination of the Zr content in the obtained $Hf(OnPr)_4$ by means of UV-VIS absorption spectrum analysis, the Zr contents were 700 ppm, 1000 ppm, 1500 ppm, 2000 ppm and more than 2000 ppm, respectively. These $Hf(OnPr)_4$ were used as the hafnium-containing materials for film formation.

Examples 32 to 36

Each $Hf(OiBu)_4$ was prepared in the same manner as in Examples 22 to 26, except that n-butyllithium was replaced by i-butyl lithium. As a result of determination of the Zr content in the obtained $Hf(OiBu)_4$ by means of UV-VIS absorption spectrum analysis, the Zr contents were 650 ppm, 200 ppm, 100 ppm, 50 ppm and 20 ppm, respectively. These $Hf(OiBu)_4$ were used as the hafnium-containing materials for film formation.

Comparative Examples 17 to 21

Each $Hf(OiBu)_4$ was prepared in the same manner as in Example 32, except that UV light irradiation time was varied to 1 minutes, 40 seconds, 30 seconds, 20 seconds and 10 seconds. As a result of determination of the Zr content in the obtained $Hf(OiBu)_4$ by means of UV-VIS absorption spectrum analysis, the Zr contents were 700 ppm, 1000 ppm, 1500 ppm, 2000 ppm and more than 2000 ppm, respectively. These $Hf(OiBu)_4$ were used as the hafnium-containing materials for film formation.

Examples 37 to 41

Each $Hf(OtBu)_4$ was prepared in the same manner as in Examples 22 to 26, except that n-butyllithium was replaced by t-butyl lithium. As a result of determination of the Zr content in the obtained $Hf(OtBu)_4$ by means of UV-VIS absorption spectrum analysis, the Zr contents were 650 ppm, 200 ppm, 100 ppm, 50 ppm and 20 ppm, respectively. These $Hf(OtBu)_4$ were used as the hafnium-containing materials for film formation.

Comparative Examples 22 to 26

Each $Hf(OtBu)_4$ was prepared in the same manner as in Example 37, except that UV light irradiation time was varied to 1 minutes, 40 seconds, 30 seconds, 20 seconds and 10 seconds. As a result of determination of the Zr content in the obtained $Hf(OtBu)_4$ by means of UV-VIS absorption spectrum analysis, the Zr contents were 700 ppm, 1000 ppm, 1500 ppm, 2000 ppm and more than 2000 ppm, respectively. These $Hf(OtBu)_4$ were used as the hafnium-containing materials for film formation.

Comparative Evaluation 5

By using each of the hafnium-containing materials obtained in Examples 22 to 41 and Comparative Examples 7 to 26, performed were a film thickness test per film formation time and a test for determination of step coverage.

First, silicon substrates having Pt film with thickness 20 nm and $SiO_2$ film with thickness 5000 Å over surface thereof were prepared five by five and mounted in the film formation chamber of the MOCVD apparatus as shown in FIG. 5. Next, temperature of the substrate was set to be 700° C. while vaporization temperature to be 70° C., and pressure to be about 266 Pa (2 Torr). $O_2$ gas was used as the reaction gas with 1000 ccm of partial pressure. Subsequently, Ar gas was used as the carrier gas and the solution material was supplied at a flow rate of 0.1 cc/min. When the film formation time reached to 1, 5, 10, 20 and 30 minutes, the sheets were taken out one by one from the film formation chamber.

(1) Film Thickness Test Per Film Formation Time

The hafnium oxide thin film over the substrate after completion of the film formation was determined for film thickness from SEM (Scanning Electron Microscope) image.

(2) Test for Step Coverage

The hafnium oxide thin film over the substrate after completion of the film formation was determined for step coverage from SEM (Scanning Electron Microscope) image. The step coverage is represented by a/b value when the substrate 61 having level difference such as grooves shown in FIG. 6 is coated with a thin film 62. If the a/b value is 1.0, it is considered that the step coverage is excellent because inner portions of grooves in the substrate as well as flat portion thereof were uniformly coated with the thin film. On the contrary, if the a/b is less than 1.0 the inner portions of the grooves has a film formation level greater than for the flat portion of the substrate. Whereas the a/b is more than 1.0, it is difficult to accomplish the film formation even for the inner portions of the substrate, thereby resulting in poor step coverage.

Evaluation

Table 7 shows the results of the hafnium-containing materials for film formation obtained in Examples 22 to 26 and Comparative Examples 7 to 11. Table 8 shows the results of the hafnium-containing materials for film formation obtained in Examples 27 to 31 and Comparative Examples 12 to 16. Table 9 shows the results of the hafnium-containing materials for film formation obtained in Examples 32 to 36 and Comparative Examples 17 to 21. Table 10 shows the results of the hafnium-containing materials for film formation obtained in Examples 37 to 41 and Comparative Examples 22 to 26, respectively.

TABLE 7

| | Organohafnium compound | Zr content (ppm) | Film thickness per film formation time (nm) | | | | | Step coverage (−) | | | | |
|---|---|---|---|---|---|---|---|---|---|---|---|---|
| | | | 1 min | 5 min | 10 min | 20 min | 30 min | 1 min | 5 min | 10 min | 20 min | 30 min |
| Ex. 22 | Hf(OnBu)$_4$ | 650 | 1.2 | 6 | 12 | 24 | 35 | 1 | 0.9 | 1 | 0.9 | 0.9 |
| Ex. 23 | Hf(OnBu)$_4$ | 200 | 1.5 | 7 | 14 | 27 | 40 | 0.9 | 0.8 | 0.8 | 1 | 0.9 |
| Ex. 24 | Hf(OnBu)$_4$ | 100 | 1 | 6 | 10 | 20 | 31 | 0.9 | 0.8 | 0.8 | 0.8 | 0.9 |
| Ex. 25 | Hf(OnBu)$_4$ | 50 | 1.3 | 6 | 12 | 22 | 34 | 0.9 | 1 | 1 | 1 | 1 |
| Ex. 26 | Hf(OnBu)$_4$ | 20 | 1.5 | 8 | 14 | 26 | 41 | 1 | 0.9 | 0.9 | 1 | 0.9 |
| Comp. Ex. 7 | Hf(OnBu)$_4$ | 700 | 0.1 | 1 | 0.9 | 0.3 | 0.01 | 0.1 | 0.1 | 0.01 | 0.02 | 0.001 |
| Comp. Ex. 8 | Hf(OnBu)$_4$ | 1000 | 1 | 1 | 0.6 | 0.07 | 0.03 | 0.2 | 0.2 | 0.01 | 0.01 | 0.003 |
| Comp. Ex. 9 | Hf(OnBu)$_4$ | 1500 | 1.3 | 0.8 | 0.5 | 0.03 | 0.01 | 0.1 | 0.2 | 0.01 | 0.02 | 0.001 |
| Comp. Ex. p10 | Hf(OnBu)$_4$ | 2000 | 1.8 | 0.3 | 0.3 | 0.04 | 0.01 | 0.1 | 0.1 | 0.02 | 0.001 | 0.002 |
| Comp. Ex. 11 | Hf(OnBu)$_4$ | >2000 | 1.2 | 1 | 0.2 | 0.01 | 0.02 | 0.1 | 0.2 | 0.01 | 0.001 | 0.001 |

TABLE 8

| | Organohafnium compound | Zr content (ppm) | Film thickness per film formation time (nm) | | | | | Step coverage (−) | | | | |
|---|---|---|---|---|---|---|---|---|---|---|---|---|
| | | | 1 min | 5 min | 10 min | 20 min | 30 min | 1 min | 5 min | 10 min | 20 min | 30 min |
| Ex. 27 | Hf(OnPr)$_4$ | 650 | 1.2 | 6 | 12 | 24 | 35 | 0.9 | 0.9 | 0.9 | 1 | 1 |
| Ex. 28 | Hf(OnPr)$_4$ | 200 | 1.7 | 8 | 16 | 30 | 45 | 1 | 1 | 0.8 | 1 | 0.9 |
| Ex. 29 | Hf(OnPr)$_4$ | 100 | 1.2 | 7 | 10 | 20 | 30 | 1 | 0.9 | 1 | 1 | 0.8 |
| Ex. 30 | Hf(OnPr)$_4$ | 50 | 0.9 | 5 | 10 | 21 | 29 | 0.8 | 1 | 0.9 | 0.8 | 0.8 |
| Ex. 31 | Hf(OnPr)$_4$ | 20 | 0.8 | 4 | 8 | 15 | 24 | 0.9 | 1 | 0.9 | 1 | 1 |
| Comp. Ex. 12 | Hf(OnPr)$_4$ | 700 | 0.5 | 1 | 0.8 | 0.2 | 0.07 | 0.5 | 0.1 | 0.02 | 0.03 | 0.02 |
| Comp. Ex. 13 | Hf(OnPr)$_4$ | 1000 | 0.5 | 2 | 1.5 | 1 | 0.6 | 0.2 | 0.05 | 0.01 | 0.01 | 0.01 |
| Comp. Ex. 14 | Hf(OnPr)$_4$ | 1500 | 0.7 | 1 | 0.6 | 0.1 | 0.03 | 0.2 | 0.08 | 0.02 | 0.01 | 0.001 |

TABLE 8-continued

| | Organohafnium compound | Zr content (ppm) | Film thickness per film formation time (nm) | | | | | Step coverage (–) | | | | |
|---|---|---|---|---|---|---|---|---|---|---|---|---|
| | | | 1 min | 5 min | 10 min | 20 min | 30 min | 1 min | 5 min | 10 min | 20 min | 30 min |
| Comp. Ex. 15 | Hf(OnPr)$_4$ | 2000 | 0.5 | 0.2 | 0.3 | 0.05 | 0.05 | 0.1 | 0.2 | 0.01 | 0.002 | 0.002 |
| Comp. Ex. 16 | Hf(OnPr)$_4$ | >2000 | 0.3 | 0.2 | 0.2 | 0.04 | 0.02 | 0.1 | 0.1 | 0.01 | 0.001 | 0.001 |

TABLE 9

| | Organohafnium compound | Zr content (ppm) | Film thickness per film formation time (nm) | | | | | Step coverage (–) | | | | |
|---|---|---|---|---|---|---|---|---|---|---|---|---|
| | | | 1 min | 5 min | 10 min | 20 min | 30 min | 1 min | 5 min | 10 min | 20 min | 30 min |
| Ex. 32 | Hf(OiBu)$_4$ | 650 | 1.1 | 4.6 | 11 | 20 | 30 | 0.8 | 1 | 1 | 1 | 0.9 |
| Ex. 33 | Hf(OiBu)$_4$ | 200 | 1.2 | 6 | 12 | 21 | 35 | 0.9 | 1 | 0.9 | 1 | 0.8 |
| Ex. 34 | Hf(OiBu)$_4$ | 100 | 0.9 | 4.5 | 9 | 19 | 26 | 1 | 0.8 | 0.8 | 0.9 | 0.8 |
| Ex. 35 | Hf(OiBu)$_4$ | 50 | 0.8 | 4 | 8 | 17 | 25 | 1 | 0.9 | 0.8 | 1 | 1 |
| Ex. 36 | Hf(OiBu)$_4$ | 20 | 1 | 4.8 | 10 | 20 | 31 | 0.9 | 0.9 | 0.9 | 0.8 | 1 |
| Comp. Ex. 17 | Hf(OiBu)$_4$ | 700 | 0.6 | 0.8 | 0.5 | 0.2 | 0.2 | 0.2 | 0.04 | 0.03 | 0.02 | 0.001 |
| Comp. Ex. 18 | Hf(OiBu)$_4$ | 1000 | 0.5 | 0.8 | 0.3 | 0.1 | 0.06 | 0.2 | 0.03 | 0.04 | 0.02 | 0.002 |
| Comp. Ex. 19 | Hf(OiBu)$_4$ | 1500 | 0.9 | 1.2 | 0.2 | 0.3 | 0.04 | 0.1 | 0.05 | 0.07 | 0.01 | 0.001 |
| Comp. Ex. 20 | Hf(OiBu)$_4$ | 2000 | 1 | 1.4 | 0.9 | 0.3 | 0.01 | 0.1 | 0.08 | 0.03 | 0.01 | 0.006 |
| Comp. Ex. 21 | Hf(OiBu)$_4$ | >2000 | 1 | 1.2 | 0.5 | 0.1 | 0.06 | 0.2 | 0.08 | 0.01 | 0.009 | 0.007 |

TABLE 10

| | Organohafnium compound | Zr content (ppm) | Film thickness per film formation time (nm) | | | | | Step coverage (–) | | | | |
|---|---|---|---|---|---|---|---|---|---|---|---|---|
| | | | 1 min | 5 min | 10 min | 20 min | 30 min | 1 min | 5 min | 10 min | 20 min | 30 min |
| Ex. 37 | Hf(OtBu)$_4$ | 650 | 1.1 | 5.2 | 10 | 20 | 30 | 0.9 | 1 | 0.9 | 1 | 0.8 |
| Ex. 38 | Hf(OtBu)$_4$ | 200 | 1.2 | 6 | 11 | 21 | 31 | 0.9 | 0.9 | 1 | 0.9 | 0.8 |
| Ex. 39 | Hf(OtBu)$_4$ | 100 | 1 | 5.1 | 9 | 18 | 28 | 0.9 | 0.8 | 0.8 | 0.8 | 0.9 |
| Ex. 40 | Hf(OtBu)$_4$ | 50 | 0.8 | 4 | 9 | 17 | 27 | 0.8 | 1 | 0.8 | 1 | 1 |
| Ex. 41 | Hf(OtBu)$_4$ | 20 | 0.9 | 4.3 | 10 | 20 | 30 | 0.9 | 1 | 0.9 | 0.9 | 0.9 |
| Comp. Ex. 22 | Hf(OtBu)$_4$ | 700 | 0.2 | 0.2 | 0.3 | 0.2 | 0.01 | 0.6 | 0.06 | 0.08 | 0.01 | 0.002 |
| Comp. Ex. 23 | Hf(OtBu)$_4$ | 1000 | 0.5 | 0.7 | 0.6 | 0.3 | 0.01 | 0.2 | 0.07 | 0.09 | 0.003 | 0.004 |
| Comp. Ex. 24 | Hf(OtBu)$_4$ | 1500 | 0.4 | 0.6 | 0.6 | 0.2 | 0.03 | 0.4 | 0.02 | 0.04 | 0.006 | 0.007 |

TABLE 10-continued

| | Organohafnium compound | Zr content (ppm) | Film thickness per film formation time (nm) | | | | | Step coverage (−) | | | | |
|---|---|---|---|---|---|---|---|---|---|---|---|---|
| | | | 1 min | 5 min | 10 min | 20 min | 30 min | 1 min | 5 min | 10 min | 20 min | 30 min |
| Comp. Ex. 25 | Hf(OtBu)$_4$ | 2000 | 0.8 | 0.8 | 0.5 | 0.02 | 0.02 | 0.6 | 0.03 | 0.03 | 0.005 | 0.002 |
| Comp. Ex. 26 | Hf(OtBu)$_4$ | >2000 | 0.5 | 1 | 0.9 | 0.01 | 0.01 | 0.7 | 0.07 | 0.04 | 0.001 | 0.003 |

As clearly shown from the above Tables 7 to 10, it was clearly found that the thin film obtained using the hafnium-containing materials for film formation in Comparative Examples 7 to 26 did not exhibit increase of thickness of the film even when time passed, and thus, it had poor stability in film formation. Also, it showed the result that the step coverage is extremely poor. Therefore, it is apprehended that if a gate oxide film is formed over the substrate having grooves by using the hafnium-containing materials for the film formation obtained in Comparative Examples 7 to 26, it causes generation of voids on the surface. While, the thin film which was formed using the hafnium-containing materials for film formation obtained in Examples 22 to 41 had extremely higher film formation rate and uniform thickness per film formation time, compared to the materials according to Comparative Examples 7 to 26. As a result, the thin film showed the improved film formation stability. Furthermore, the thin film was uniformly coated in even inner portion of the grooves as well as the flat portions of the substrate since the value of the step coverage was close to 1.0.

What is claimed is:

1. A hafnium-containing material for film formation, said material comprising an organohafnium compound with zirconium in the material being 650 ppm or less and 50 ppm or more.

2. The material according to claim 1, wherein the organohafnium compound has a bond of a hafnium atom with a nitrogen atom.

3. The material according to claim 2, wherein the organohafnium compound has the following formula:

$$\mathrm{Hf}(R^1R^2N)_4 \qquad (1)$$

wherein $R^1$ and $R^2$ each represents a straight-chain or branched alkyl group having 1 to 4 carbon atoms and $R^1$ and $R^2$ are the same or different from each other.

4. The material according to claim 3, wherein the organohafnium compound is $\mathrm{Hf}[(C_2H_5)_2N]_4$, $\mathrm{Hf}[(CH_3)_2N]_4$ or $\mathrm{Hf}[(CH_3)(C_2H_5)N]_4$.

5. The material according to claim 1, wherein the organohafnium compound has a bond of a hafnium atom with an oxygen atom.

6. The material according to claim 5, wherein the organohafnium compound has the following formula:

$$\mathrm{Hf}(OR^3)_4 \qquad (2)$$

wherein $R^3$ represents a straight-chain or branched alkyl group having 1 to 4 carbon atoms.

7. The material according to claim 6, wherein the organohafnium compound is $\mathrm{Hf}[O(n-C_4H_9)]_4$, $\mathrm{Hf}[O(t-C_4H_9)]_4$ or $\mathrm{Hf}[O(s-C_4H_9)]_4$ wherein $n-C_4H_9$ is a normal butyl group, $t-C_4H_9$ is a tert-butyl group and $s-C_4H_9$ is a sec-butyl group.

8. The material according to claim 1, wherein an alkali metal and an alkaline-earth metal in the material are 1 ppm or less, respectively.

9. The material according to claim 1, wherein the total amount of iron, zinc, titanium, aluminum, chromium, and nickel in the material is in the range from 0.1 ppm to 0.8 ppm.

10. The material according to claim 1, wherein the material further comprises an organosilicon compound having a bond of a silicon atom with a nitrogen atom, in addition to the organohafnium compound.

11. A method for producing a hafnium-containing material for film formation, comprising a process for removing impurities contained in an organohafnium compound by means of flash chromatography.

12. The method according to claim 11, wherein the process for removing impurities comprises the steps of:
charging a chelating agent-carrying filler into a pressure-resistant column to form a filler layer inside the column;
introducing the organohafnium compound from the upper portion of the filler layer; and
adsorbing the impurities contained in the organohafnium compound inside the filler layer, by supplying a predetermined flow rate of pressurized air from the upper portion of the column inside the column to pass the hafnium compound through the filler layer.

13. A method for producing a hafnium-containing material for film formation, comprising:
a process for removing impurities contained in a hafnium-containing compound by means of flash chromatography;
a process for obtaining a crude product of an organohafnium compound using the hafnium-containing compound and aminolithium; and
a reduced-pressure distillation process for distilling the crude product under reduced pressure to obtain the purified product of the compound.

14. The method according to claim 13, wherein the process for removing impurities comprises the steps of:
charging the hafnium-containing compound into a pressure-resistant column to form a filler layer inside the column;
adsorbing the impurities contained in the organohafnium compound forming the filler layer to the chelating agent, by introducing a chelating agent from the upper portion of the filler layer to pass the chelating agent through the filler layer; and
taking out the hafnium-containing compound forming the filler layer from the column, followed by washing the taken-out hafnium-containing compound with a solvent.

15. A method for producing a hafnium-containing material for film formation, comprising:
- a process for removing impurities contained in a hafnium-containing compound by means of light irradiation;
- a process for obtaining a crude product of an organohafnium compound using aminolithium and alcohol together with the hafnium-containing compound; and
- a reduced-pressure distillation process for distilling the crude product under reduced pressure to obtain the purified product of the compound.

16. The method according to claim 15, wherein the process for removing the impurities comprises the steps of:
- preparing a suspension by suspending the hafnium-containing compound in an ether solution;
- adding a sintered activated carbon to the suspension;
- adding zirconium pieces to the suspension, the zirconium pieces being subjected to electrolytic polishing followed by treating the back side thereof with hydrogen peroxide;
- irradiating the suspension to which the zirconium pieces are added, with visible light or ultraviolet (UV) light;
- removing the sintered activated carbon and the zirconium pieces from the suspension after irradiation of visible light or UV light;
- concentrating the suspension to remove an ether component in the suspension; and
- microfiltrating the concentrated solution after removal of the ether component.

17. A hafnium-containing material for film formation, said material comprising an organohafnium compound with zirconium in the material being 650 ppm or less and 50 ppm or more, dissolved in a solvent.

18. A hafnium-containing material for film formation, said material comprising an organosilicon compound having a bond of a silicon atom with a nitrogen atom, and an organohafnium compound having a zirconium content of 650 ppm or less, dissolved in a solvent.

19. A method for producing a hafnium-containing thin film, comprising forming the thin film using a material containing an organohafnium compound with zirconium in the material being 650 ppm or less and 50 ppm or more by means of Metal Organic Chemical Vapor Deposition.

20. A method for producing a hafnium-containing thin film, comprising forming the thin film using a material containing an organosilicon compound having a bond of a silicon atom with a nitrogen atom and an organohafnium compound having a zirconium content of 650 ppm or less, by means of Metal Organic Chemical Vapor Deposition.

* * * * *